United States Patent
Højgaard et al.

(10) Patent No.: US 10,912,847 B2
(45) Date of Patent: Feb. 9, 2021

(54) COMPRESSED SOLID COMPOSITION FOR MRI

(71) Applicant: Ascelia Pharma AB, Malmö (SE)

(72) Inventors: Bent Højgaard, Allerød (DK); Magnus Olafsson Corfitzen, Hellerup (DK); Dorthe Da Graca Couto Thrige, Dragør (DK)

(73) Assignee: Ascelia Pharma AB, Malmö (SE)

( * ) Notice: Subject to any disclaimer, the term of this patent is extended or adjusted under 35 U.S.C. 154(b) by 0 days.

(21) Appl. No.: 16/895,263

(22) Filed: Jun. 8, 2020

(65) Prior Publication Data

US 2020/0384129 A1 Dec. 10, 2020

(30) Foreign Application Priority Data

Jun. 7, 2019 (EP) .................... 19179015

(51) Int. Cl.
| | | |
|---|---|---|
| A61B 5/055 | (2006.01) | |
| A61K 49/18 | (2006.01) | |
| A61K 9/46 | (2006.01) | |
| A61K 9/00 | (2006.01) | |
| A61K 47/32 | (2006.01) | |
| A61K 47/38 | (2006.01) | |
| A61K 31/593 | (2006.01) | |
| A61K 47/36 | (2006.01) | |
| A61K 31/198 | (2006.01) | |
| A61K 47/02 | (2006.01) | |
| A61K 47/12 | (2006.01) | |
| A61K 47/34 | (2017.01) | |
| A61K 47/26 | (2006.01) | |

(52) U.S. Cl.
CPC ............ *A61K 49/18* (2013.01); *A61K 9/0007* (2013.01); *A61K 9/0053* (2013.01); *A61K 31/198* (2013.01); *A61K 31/593* (2013.01); *A61K 47/02* (2013.01); *A61K 47/12* (2013.01); *A61K 47/26* (2013.01); *A61K 47/32* (2013.01); *A61K 47/34* (2013.01); *A61K 47/36* (2013.01); *A61K 47/38* (2013.01); *A61K 9/0065* (2013.01)

(58) Field of Classification Search
None
See application file for complete search history.

(56) References Cited

U.S. PATENT DOCUMENTS

| | | | | |
|---|---|---|---|---|
| 5,468,504 A | * | 11/1995 | Schaeffer | A61K 31/40 424/466 |
| 5,707,654 A | | 1/1998 | Beres et al. | |
| 6,015,545 A | * | 1/2000 | Thomsen | A61K 49/06 424/639 |
| 6,136,292 A | * | 10/2000 | Pettersson | A61K 49/103 424/9.3 |

FOREIGN PATENT DOCUMENTS

| | | |
|---|---|---|
| WO | 1996/005867 A2 | 2/1996 |
| WO | 1997/02842 A1 | 1/1997 |
| WO | 1998/11922 A2 | 3/1998 |
| WO | 2005/058375 A1 | 6/2005 |
| WO | 2007/042153 A1 | 4/2007 |
| WO | 2010/099804 A1 | 9/2010 |

OTHER PUBLICATIONS https://www.amerilabtech.com/wp-content/uploads/2012/01/EffervescentTabletsKeyFacts.pdf.*
Albiin et al. (Magn. Reson. Mater. Phys. 2012, 25, 361-368).*
Aliyu, H. et al., Bayero Journal of Pure and Applied Sciences, 2(2) 191-193, Year: 2009.
Jørgensen, J. et al., Acta Radiol.,53; 707-713, Year: 2012.
Kroll, H., Manganous Complexes of Several Amino Acids, 74:2034, Year: 1950.
Mrozeka, R. et al., Polyhedron, 18: 2321-2326, Year: 1999.

* cited by examiner

*Primary Examiner* — Michael G. Hartley
*Assistant Examiner* — Melissa J Perreira
(74) *Attorney, Agent, or Firm* — Dinsmore & Shohl LLP; Weston R. Gould

(57) ABSTRACT

The present invention relates to a compressed solid composition for MRI comprising a physiologically acceptable manganese (II) compound, its preparation and use for preparing an oral solution.

18 Claims, 2 Drawing Sheets

COMPRESSED SOLID COMPOSITION FOR MRI

REFERENCE TO RELATED APPLICATION

This application claims priority to European application No. 19179015.3, filed Jun. 7, 2019, the entire content of which is incorporated herein by reference.

TECHNICAL FIELD

The present invention relates to a compressed solid composition for magnetic resonance imaging (MRI) comprising a physiologically acceptable manganese (II) compound, its preparation and use for preparing an oral solution.

BACKGROUND

Manganese is one of the most abundant metals on earth and is found as a component of more than 100 different minerals. Besides being an essential trace element in relation to the metabolic processes in the body, manganese is also a paramagnetic metal that possesses characteristics similar to gadolinium with regard to T1-weighted (T1-w) magnetic resonance imaging (MRI). Manganese, in the form of manganese (II) chloride tetrahydrate, is the active substance in the targeted oral contrast agent, Mangoral, indicated for hepatobiliary MRI. Under physiological circumstances manganese is poorly absorbed from the intestine after oral intake, but by the use of specific absorption promoters, L-alanine and vitamin D3, it is possible to obtain a sufficiently high concentration in the liver in order to achieve a significant signal enhancing effect. In the liver manganese is exposed to a very high first-pass effect, up to 98%, which prevents the metal from reaching the systemic circulation, thereby reducing the number of systemic side effects. Manganese is one of the least toxic trace elements, and due to its favorable safety profile it may be an attractive alternative to gadolinium-based contrast agents for patients undergoing an MRI evaluation of the liver in the future, in particular for patients with severe renal insufficiency or acute kidney injury.

Liver metastases are the most frequent type of malignant focal liver lesion. Metastasis to the liver often occurs in progressive cancer disease and is associated with substantially reduced survival. In fact, the liver is one of the most frequent—and often the first—site of metastasis. About 70% of all patients with colorectal cancer will develop liver metastases at some point in their lifetime, and one-third of these will have metastases confined only to the liver. Early detection and localization of liver metastases is critical for optimal patient management. Mangoral is the first contrast agent in the world to obtain Orphan Drug Designation by the FDA for use in liver MRI in patients where use of gadolinium-based contrast agents may be medically inadvisable, or where gadolinium-based contrast agents cannot be administered.

Mangoral is orally administered and consists of manganese combined with absorption promoters to increase manganese absorption in the small intestine, a prerequisite for a high uptake of manganese into the liver tissue, which is the optimal condition for obtaining high imaging quality. Manganese is a natural trace element and after absorption from the gastrointestinal tract it is efficiently taken up by hepatocytes. Due to the retention of manganese in the hepatocytes and its paramagnetic properties, the contrast agent clearly enhances the liver tissue in MR imaging whilst the liver metastases do not accumulate manganese. Therefore, the liver metastases will become clearly detectable against the enhanced liver tissue on the MR image.

Currently, Mangoral is provided in two-compartment powder formulation, with the manganese salt in one sachet, and one or more absorption promoters in a separate sachet because the powders are considered incompatible. The two sachets are then emptied into a glass of water to provide the oral MRI solution.

Although the two-compartment formulation works well, a compressed solid composition comprising the active ingredients of Mangoral would ease the patients' handling of the compressed solid composition and would potentially allow for home administration with lower risk of incorrect dosing of the contrast composition and thereby reduce hospital stay in connection with MRI. Hence, there is a need in the art for the provision of a single-compartment formulation of Mangoral, particularly in the form of a compressed solid composition.

SUMMARY

The present inventors have found that the active ingredients of Mangoral can be prepared in a single-compartment formulation as a compressed solid composition for MRI, which is suitable for preparing an oral solution. By preparing the compressed solid composition at low relative humidity (rH), such as below 25% rH, and by carefully selecting water-soluble excipients having low hygroscopicity, the present inventors have successfully prepared water-soluble tablets and effervescent tablets comprising manganese (II) chloride.

In a first aspect, a magnetic resonance imaging (MRI) contrast composition is provided comprising: a physiologically acceptable manganese (II) compound, one or more absorption promoters, and one or more water-soluble excipients, wherein the compressed solid composition is a compressed solid composition suitable for preparing an oral solution.

In a second aspect, a method for preparing the compressed solid composition as defined herein is provided, wherein the method comprises the steps of:
 a. Providing a physiologically acceptable manganese (II) compound, optionally as a granulate, and optionally drying the physiologically acceptable manganese (II) compound;
 b. providing one or more absorption promoters;
 c. providing one or more water-soluble excipients allowing for compression;
 d. Mixing the physiologically acceptable manganese (II) compound with the one or more absorption promoters and the one or more water-soluble excipients to provide a water-soluble mixture; and
 e. Compressing the water-soluble mixture to provide a compressed solid composition as defined herein.

In a third aspect, a compressed solid composition prepared by the method defined herein is provided.

In a fourth aspect, a method for preparing an oral MRI solution is provided comprising:
 a. providing a compressed solid composition as defined herein,
 b. providing a suitable amount of water, and
 c. adding said compressed solid composition to said water, thereby forming the oral MRI solution.

DESCRIPTION OF DRAWINGS

FIG. 3A shows an effervescent tablet providing a clear solution after 5 minutes without any precipitate; FIG. 3B shows a two-compartment powder formulation providing a clear solution with a precipitate after 5 minutes.

DEFINITIONS

Figure 1:
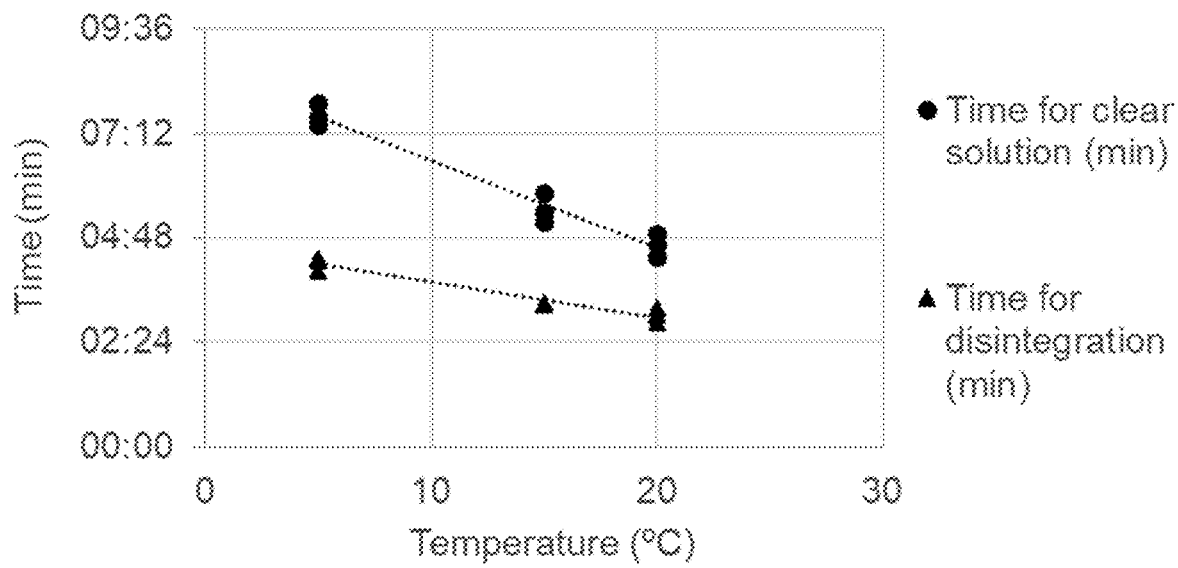
FIG. 1: Temperature effect on effervescent tablets (water volume 200 ml). The effervescent tablets quickly disintegrate and the dissolution time decreases with increasing temperature.

The term "water-soluble" is used herein to describe a compound that dissolve in water at room temperature, such as about 25° C. The extent of water-solubility ranges widely, from infinitely soluble (without limit) (fully miscible) such as ethanol in water, to poorly soluble, such as silver chloride in water. The term insoluble is often applied to poorly or very poorly soluble compounds.

The term "water-insoluble" is used herein to describe a compound that does not dissolve in water at room temperature, such as about 25° C.

A number of other descriptive terms are also used to quantify the extent of solubility for a given solute, i.e. the compound subject to solution:

| Term | Mass parts of water required to dissolve 1 mass part of solute |
|---|---|
| Very soluble | <1 |
| Freely soluble | 1 to 10 |
| Soluble | >10 to 30 |
| Sparingly soluble | >30 to 100 |
| Slightly soluble | >100 to 1000 |
| Very slightly soluble | >1000 to 10,000 |
| Practically insoluble or insoluble | >10,000 |

The water-solubility of a given solute typically depends on temperature. Depending on the nature of the solute the solubility may increase or decrease with temperature. For most solids and liquids, their solubility in water increases with temperature.

The term "poor solubility in cold water" is used herein to describe a compound that does not dissolve completely in cold water, such as a glass of water, such as between about 2 to about 15° C.

The terms "dissolve slowly" and "dissolve very slowly" are used herein to describe a compound that has a low rate of solubilization in water. A "low rate" in the present context shall mean any rate that does not allow for full solubilization of the compound in water, such as a glass of water, within 8 minutes or less.

The term "hygroscopic" is used herein to describe a compound that sorbs water, either by absorption, adsorption, or a combination of the two processes at between 40 and 60% relative humidity (rH) to any significant extent, such as to the extent wherein the mass and/or volume of said compound increases by about 5% or more within a period of time, such as after about 1 hour.

The term "relative humidity" or "rH" refers to the ratio in percentage of the partial pressure of water vapor to the equilibrium vapor pressure of water at a given temperature.

The term "non-hygroscopic water soluble" is used herein to describe a compound that is not hygroscopic in accordance with the definition herein, and at the same time is water-soluble according to the definition herein.

The term "absorption promoter" is used herein interchangeably with the term "uptake promoter" which refers to a compound capable of enhancing manganese transport across the membranes of the gastrointestinal tract. These compounds are well known in the art from e.g. WO 96/05867 and comprise physiologically tolerable reducing compounds containing an α-hydroxy ketone group, a physiologically tolerable acid containing α- and/or β-hydroxy or amino groups, or a salt thereof, and/or vitamin D.

The term "effervescent couple" as used herein refers to a pair of pharmaceutically acceptable excipients, one of which is a basic ingredient and the other is an acidic ingredient. The basic ingredient liberates carbon dioxide when it comes in contact with the acidic ingredient and water. An example of the basic ingredient is bicarbonate.

The term "clear solution" as used herein refers to a solution which appears transparent upon visual inspection in daylight.

DETAILED DESCRIPTION

The present disclosure provides a magnetic resonance imaging (MRI) contrast composition comprising: a physiologically acceptable manganese (II) compound, one or more absorption promoters, and one or more water-soluble excipients, wherein the compressed solid composition is a compressed solid composition suitable for preparing an oral solution.

Difficulties in Production of Compressed Hygroscopic Solids

The design and manufacture of pharmaceutical compressed solids, such as tablets, is a complex multi-stage process wherein several parameters need careful control, i.e. delivering the correct amount of drug substance in the right formulation, at the appropriate time, at the proper rate and at the desired location with its chemical integrity protected throughout the process.

Primary goals of a tablet manufacturing process include:
To formulate tablets that are strong and hard to withstand mechanical shock encountered during manufacturing, packing, shipping, dispensing and use.
To formulate tablets that are uniform in weight and in drug content.
To formulate tablets that are bioavailable according to indication requirements.
To formulate tablets that are chemically and physically stable over a long period of time.
To formulate tablets that have elegant product identity which is free from any tablet defects.

During tablet compression, it is generally preferred to have a relatively higher moisture content so that higher tablet hardness can be produced at lower compression force. There is a limit though, because higher moisture content tends to produce two detrimental results:
An increase in moisture causes a reduction in powder flow rate, which then increases powder particle adhesion, leading to erratic tablet weight uniformity.

An increase in moisture causes an increase in sticking defects, which can be particularly challenging with embossed compression tooling because there are more pockets where powder may adhere.

Regarding chemical stability, a relatively lower moisture content is preferred to reduce the extent of drug degradation, make it more difficult for microbial growth to occur, and prevent clogging of the compounds. Effervescent tablets, for example, are very sensitive to moisture content. The chemical reaction between the organic acid and inorganic base is autocatalytic and it yields gaseous carbon dioxide and water. A very low moisture content is, therefore, required to prevent the reaction from starting, but once started, the water produced by it further promotes the reaction until the components are exhausted.

For hygroscopic materials, tablet production can be very difficult and require careful optimization of the excipient selection as well as the tabletting process.

Hygroscopy

Hygroscopy is the phenomenon of attracting and holding water molecules from the surrounding environment, which is usually at normal or room temperature. This is achieved through either absorption or adsorption with the adsorbing substance becoming physically changed. This could be an increase in volume, boiling point, viscosity, or other physical characteristic or property of the substance, as water molecules can become suspended between the substance's molecules in the process.

The total amount of water, which can be taken up by a hygroscopic material will be a function of the temperature and humidity of the atmosphere in which it is located and will ultimately be determined by the sorption isotherm of the system.

The term "hygroscopic" is used herein to describe a compound that sorbs water, either by absorption, adsorption, or a combination of the two processes at between 40 and 60% relative humidity (rH) to any significant extent, such as to the extent where the mass and/or volume of said compound increases by about 5% or more after a period of time, such as after about 1 hour.

Relative Humidity (rH)

Poor environmental control, particularly in terms of air humidity can directly affect the pharmaceutical production line in a number of ways. Levels of humidity below 45% rH will allow electrostatic charges to build up in machinery and materials. This can have major implications where flammable solvents are used in the process, so that electrical bonding between machines becomes important. Low humidity can also cause the product to dry out, affecting its performance. Build-up of charge on powders can result in poor power flow, and charged products can cause them to stick to each other, leading to packing problems.

High humidity can also cause products to absorb moisture during production and final packaging. Where the product is long-term moisture sensitive it will degrade over time when packed under the wrong conditions.

The issue of humidity is complex, since there may well be different requirements for the moisture content of atmospheres at different steps in the manufacturing process.

Air conditioning and handling equipment based on refrigeration cycles—heating ventilation and air conditioning (HVAC) systems, is generally built to condition working environments so as to maintain levels of relative humidity between 40 and 60%, with temperatures around 21-25° C.

In the context of the present disclosure, it is important to control the relative humidity to below 35% rH, such as below 34%, such as below 33%, such as below 32%, such as below 31%, such as below 30%, such as below 29%, such as below 28%, such as below 27%, such as below 26%, such as below 25%, such as below 24%, such as below 23%, such as below 22%, such as below 21%, such as below 20%, such as below 19%, such as below 18%, such as below 17%, such as below 16%, such as below 15%, such as below 14%, such as below 13%, such as below 12%, such as below 11%, such as below 10% of the atmosphere in all of the tablet production areas.

In one embodiment the relative humidity (rH) is kept below 30%. In one embodiment the relative humidity (rH) is kept below 25%. In one embodiment the relative humidity (rH) is kept below 20%. In one embodiment, the relative humidity (rH) is kept below 15%, such as below 10%.

Relative humidity levels below 40% can be achieved with a rotary dessicant dryer. These machines have been in use for many years and can be sized according to the work area that needs to be dried. They function by passing a stream of ambient air through a solid dessicant (typically silica gel) located within a rotating wheel or bed. The exit air from the rotary dryer may have a relative humidity of 1% or lower, and it may be necessary to blend this air stream with another to achieve the required level of humidity for the particular manufacturing equipment or process. Flow control is therefore important. Water that is absorbed from the air by the dessicant is released by the dessicant bed rotating into a stream of hot air. The resulting wet air is usually vented outside the building.

Pharmaceutical Excipients

A pharmaceutical excipient is a substance formulated alongside the active ingredient of a medicament, included for the purpose of long-term stabilization, bulking up solid formulations that contain potent active ingredients in small amounts (thus often referred to as "bulking agents", "fillers", or "diluents"), or to confer a therapeutic enhancement on the active ingredient in the final dosage form, such as but not limited to facilitating drug absorption, reducing viscosity, or enhancing solubility. Pharmaceutical excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

It will be understood by a person of skill in the art, that while some excipients are preferred and some are not preferred to include in the compositions as disclosed herein, it may be possible to produce a tablet comprising a non-preferred excipient if the relative amount of that excipient is carefully controlled. Some excipients may comprise about 5% moisture and thus be non-preferred, but may still be included in low amounts, if the other excipients included are non-hygroscopic and dry. The following section outlines different groups of excipients according to the present disclosure and pointers to which excipients are preferred to include in the mixing blend to provide a compressed solid composition with desired properties.

In one embodiment, the compressed solid composition is provided as defined herein, wherein the one or more water-soluble excipients are non-hygroscopic water-soluble excipients. In one embodiment, the one or more water-soluble excipients are selected from the group consisting of: a non-hygroscopic filler, a non-hygroscopic binder, a non-hygroscopic disintegrant, and a non-hygroscopic lubricant.

The excipients of the present disclosure should collectively allow for:

Efficient production of a plurality of compressed solid compositions (tablets) being uniform in size and all comprising essentially the same amount of the active ingredients (manganese (II) compound and absorption promoter(s)).

Fast and essentially complete dissolution of the compressed solid composition in water without agitation or stirring.

The formation of a clear oral solution having an acceptable taste for oral consumption.

Fillers/diluents: a "filler" or a "diluent" according to the present disclosure is preferably a water-soluble and non-hygroscopic filler. In one embodiment, the compressed solid composition is provided as defined herein, wherein the non-hygroscopic filler is selected from the group consisting of: isomalt; lactose, such as spray-dried lactose, α-lactose, or β-lactose; maltitol; maltose; and mannitol.

Dextrin and lactitol may be used as alternative fillers in low amounts but typically contain 5% moisture and hence, are not preferred to include.

Dextrates, dextrose, fructose, hypromellose, maltodextrin, sucrose, sorbitol and xylitol are also water-soluble fillers but are all hygroscopic and thus not preferred to include in the compressed solid compositions as defined herein. In one embodiment, the compressed solid composition is provided as defined herein, wherein the compressed solid composition does not comprise a hygroscopic filler selected from the group consisting of: a dextrate, dextrose, fructose, hypromellose, maltodextrin, sucrose, sorbitol and xylitol.

In one embodiment, the compressed solid composition does not comprise a water-insoluble filler. In one embodiment, the water-insoluble filler is selected from the group consisting of: calcium carbonate, calcium phosphate (e.g. basic calcium phosphate, calcium hydrogen phosphate, dicalcium phosphate), calcium silicate, cellulose powdered, cellulose acetate, magnesium carbonate, magnesium oxide, medium-chain triglycerides, microcrystalline cellulose, silicified microcrystalline cellulose, polymethacrylates, starch, calcium sulfate, and pregelatinized starch. In one embodiment, the compressed solid composition is provided as defined herein, wherein the compressed solid composition does not comprise a water-insoluble filler selected from the group consisting of: calcium carbonate; calcium phosphate, such as basic calcium phosphate, calcium hydrogen phosphate, or dicalcium phosphate; calcium silicate; cellulose powder; cellulose acetate; magnesium carbonate; magnesium oxide; a medium-chain triglyceride; microcrystalline cellulose; silicified microcrystalline cellulose; a polymethacrylate; starch; calcium sulfate; and pregelatinized starch.

Binders: a "binder" according to the present disclosure is preferably a water-soluble and non-hygroscopic binder. In one embodiment, the water-soluble and non-hygroscopic binder is selected from the group consisting of: hydroxyethylmethyl cellulose, maltose, povidone, and dextrin. In one embodiment, the binder is povidone.

Carboxymethylcellulose sodium, dextrates, dextrose, hydroxyethyl cellulose, hydroxypropyl cellulose, maltodextrin, poloxamer, polydextrose and sucrose may be used as alternative water-soluble binders in low amounts but are all hygroscopic and thus not preferred.

Acacia, hypromellose, methylcellulose and sodium alginate are water-soluble but dissolve very slowly in water and are not very useful. Pre-gelatinized starch, inulin, agar, gelatin, starch, alginic acid, cellulose acetate phthalate, ethylcellulose, hydrogenated vegetable oil, magnesium aluminum silicate, microcrystalline cellulose, and polymethacrylates have poor solubility in cold water and hence, are not preferred binders.

In one embodiment, the compressed solid composition is provided as defined herein, wherein compressed solid composition does not comprise a poorly water-soluble binder selected from the group consisting of: acacia, hypromellose, methylcellulose, sodium alginate, pre-gelatinized starch, inulin, agar, gelatin, starch, alginic acid, cellulose acetate phthalate, ethylcellulose, hydrogenated vegetable oil, magnesium aluminum silicate, microcrystalline cellulose, and polymethacrylate.

Disintegrants: a "disintegrant" is known in the art to expand and dissolve when wet causing the compressed pharmaceutical composition, such as a tablet, to break apart.

Povidone is a water-soluble disintegrant, but not a very strong disintegrant. In one embodiment, the compressed solid composition is provided comprising a non-hygroscopic disintegrant, wherein the non-hygroscopic disintegrant is povidone.

Carboxymethylcellulose calcium, croscarmellose sodium, and crospovidone are insoluble in water, but very strong disintegrants and may be applied in very low levels and are preferred. In one embodiment, the compressed solid composition is provided as defined herein, further comprising a water-insoluble disintegrant. In one embodiment, the water-insoluble disintegrant is selected from the group consisting of: carboxymethylcellulose calcium; croscarmellose sodium; and crospovidone.

Carboxymethylcellulose sodium and hydroxypropyl cellulose are water-soluble disintegrants but are not preferred as they are hygroscopic. In one embodiment, the compressed solid composition does not comprise a hygroscopic disintegrant selected from the group consisting of: carboxymethylcellulose sodium and hydroxypropyl cellulose.

Methylcellulose, sodium alginate, pregelatinized starch, starch, alginic acid, calcium alginate, magnesium aluminum silicate, microcrystalline cellulose, polacrilin potassium, and sodium starch glycolate can be applied as disintegrants but are not preferred as they dissolve slowly or are insoluble in water and need to be added in high levels.

Lubricants: A "lubricant" prevents ingredients from sticking to and clogging the tablet punches or capsule filling machine. During tablet production, lubricants also ensure that tablet formation and ejection can occur with low friction between the solid and die wall.

Polyethylene glycol 6000 and sodium benzoate are preferred water-soluble and non-hygroscopic binders. In one embodiment, the compressed solid composition is provided as defined herein, wherein the non-hygroscopic lubricant is selected from the group consisting of: polyethylene glycol 6000 and sodium benzoate.

Sodium lauryl sulfate yields a bitter taste and hence, is not preferred.

Poloxamer and polyethylene glycol 4000 are water-soluble but hygroscopic lubricants and are not preferred. In one embodiment, the compressed solid composition is provided as defined herein, wherein the compressed solid composition does not comprise a hygroscopic lubricant selected from the group consisting of: poloxamer and polyethylene glycol 4000.

Sodium stearyl fumarate, calcium stearate, colloidal silica, glycerin monostearate, glyceryl behenate, glyceryl palmitostearate, hydrogenated castor oil, hydrogenated vegetable oil, magnesium stearate, medium-chain triglycerides, palmitic acid, stearic acid, talc, zinc stearate are all water-insoluble and thus not preferred to include in the compressed solid composition as defined herein. In one embodiment, the compressed solid composition does not comprise a water-insoluble lubricant selected from the group consisting of:

sodium stearyl fumarate, calcium stearate, colloidal silica, glycerin monostearate, glyceryl behenate, glyceryl palmitostearate, hydrogenated castor oil, hydrogenated vegetable oil, magnesium stearate, medium-chain triglycerides, palmitic acid, stearic acid, talc, and zinc stearate.

Properties of the Compressed Solid Compositions

According to the present disclosure, a carefully selected blend of water-soluble excipients that together with the physiologically acceptable manganese (II) compound and the one or more absorption promoters allow for compression into a solid composition is provided.

It is important that a plurality of tablets produced from a batch, by the methods disclosed herein, all have substantially the same amount of ingredients.

Further, dissolving the compressed solid composition in water, such as a glass of water e.g. about 0.2 L, should provide a clear solution, except for any residual vitamin D, which may or may not be present in the compressed solid composition. Vitamin D, when added to water, generally resides as an oil phase on top of the water phase. It is further desired that the dissolved solid composition has a neutral taste. In one embodiment, vitamin D is in the form of vitamin D3 100,000. In one embodiment, vitamin D3 is in the form of Dry Vitamin D3 100 SD/S.

In one embodiment, the compressed solid composition has a sufficient hardness and low moisture content. In one embodiment, the hardness of the compressed solid composition is between 35N and 110N, such as more than 40N, such as more than 45N, such as more than 50N, such as more than 55N, such as more than 60N, such as more than 65N, such as more than 70N, such as more than 75N, such as more than 80N, such as more than 85N, such as more than 90N, such as more than 95N, such as more than 100N, such as more than 105N, such about 110N.

In one embodiment, the compressed solid composition is for use in preparing an oral solution.

In one embodiment, the compressed solid composition is for use as a magnetic resonance imaging (MRI) contrast composition.

Dissolution Rate

In one embodiment, the compressed solid composition provides a clear solution in water at room temperature within 8 minutes or less, such as within 7 minutes or less, such as within 6 minutes or less, such as within 5 minutes or less, such as within 4 minutes or less, such as within 3 minutes or less, without stirring or agitation of the solution. Preferably, a clear solution is formed within 5 minutes, even more preferred within 3 minutes or less.

In one embodiment, the compressed solid composition provides a clear solution in 0.2 L water at room temperature within 8 minutes or less, such as within 7 minutes or less, such as within 6 minutes or less, such as within 5 minutes or less, such as within 4 minutes or less, such as within 3 minutes or less, without stirring or agitation of the solution. Preferably, a clear solution is formed within 5 minutes, even more preferred within 3 minutes or less.

In one embodiment, the compressed solid composition completely dissolves in water at room temperature within 8 minutes or less, such as within 7 minutes or less, such as within 6 minutes or less, such as within 5 minutes or less, such as within 4 minutes or less, such as within 3 minutes or less, without stirring or agitation of the solution. Preferably, the compressed solid composition completely dissolves in water within 5 minutes, even more preferred within 3 minutes or less.

In one embodiment, the compressed solid composition completely dissolves in cold water, such as between about 2 to about 15° C. within 8 minutes. In one embodiment, the compressed solid composition completely dissolves in 0.2L water at 5° C. within about 8 minutes.

Disintegration Rate

In one embodiment, the compressed solid composition disintegrates within less than 3.0 minutes in water at room temperature, such as within less than 2.5 minutes, such as within less than 2 minutes, such as within less than 1.5 minutes, such as within less than 1 minute, without any stirring or agitation of the solution. Preferably, the compressed solid composition disintegrates within 2 minutes, even more preferred within 1 minute or less.

In one embodiment, the compressed solid composition disintegrates within less than 3.0 minutes in 0.2 L water at room temperature, such as within less than 2.5 minutes, such as within less than 2 minutes, such as within less than 1.5 minutes, such as within less than 1 minute, without any stirring or agitation of the solution.

pH of the Resulting Solution

Effervescent tablets comprising manganese can when dispensed into water lead to formation of a precipitate consisting of manganese carbonate salts. These salts can be re-dissolved by acidifying the resulting solution, preferably by adjusting the pH of the resulting solution to between 2 and 7.

In one embodiment, the compressed solid composition results in a pH of between 2 to 7 in 0.2 L water after complete dissolution of between 0.5 g and 1 g manganese (II) chloride tetrahydrate or an equimolar amount of any corresponding manganese (II) salt.

Physiologically Acceptable Manganese (II) Compounds

In one embodiment, the compressed solid composition is provided as defined herein, wherein the physiologically acceptable manganese (II) compound is a salt of an inorganic anion or an organic anion. In one embodiment, the inorganic anion is selected from the group consisting of chloride, fluoride, bromide, iodide, sulphate, and phosphate. In one embodiment, the organic anion is selected from the group consisting of: ascorbate, kojate, salicylate, and gluconate.

In one embodiment, the compressed solid composition is provided as defined herein, wherein the physiologically acceptable manganese (II) compound is selected from the group consisting of: manganese (II) sulphate, manganese (II) gluconate, manganese (II) chloride anhydrate, manganese (II) chloride dihydrate, manganese (II) chloride tetrahydrate, and a combination thereof.

In one embodiment, the compressed solid composition is provided as defined herein, wherein the physiologically acceptable manganese (II) compound is manganese (II) chloride tetrahydrate.

In one embodiment, the compressed solid composition is provided as defined herein, wherein the compressed solid composition comprises between 0.5 g and 1.2 g manganese (II) chloride tetrahydrate or an equimolar amount of any corresponding manganese (II) salt.

In one embodiment, the compressed solid composition is provided as defined herein, wherein the compressed solid composition comprises between 0.6 g and 1 g of manganese (II) chloride tetrahydrate, such as between 0.65 g and 0.95 g, such as between 0.70 g and 0.90 g, such as between 0.75 g and 0.85 g, such as 0.80 g.

In one embodiment, the compressed solid composition is provided as defined herein, wherein the compressed solid composition comprises 0.8 g manganese (II) chloride tetrahydrate or an equimolar amount of any corresponding manganese (II) salt.

In one embodiment, the compressed solid composition is provided as defined herein, wherein the compressed solid composition comprises 0.8 g manganese (II) chloride tetrahydrate or an equimolar amount of the corresponding anhydrate or dihydrate.

In one embodiment, the compressed solid composition is provided as defined herein, wherein the composition comprises:
 a) Manganese (II) chloride tetrahydrate or dihydrate;
 b) Alanine, such as L-alanine;
 c) Isomalt;
 d) Croscarmellose, such as croscarmellose sodium; and
 e) Polyethylene glycol, such as PEG6000.

In one embodiment, the compressed solid composition further comprises vitamin D, such as vitamin $D_3$.

Absorption Promoters

Under physiological circumstances the manganese of the physiologically acceptable manganese (II) compound is poorly absorbed from the intestine after oral intake, but by the use of specific absorption promoters, such as L-alanine and vitamin $D_3$, it is possible to obtain a sufficiently high concentration in the liver in order to achieve a significant signal enhancing effect during MRI.

The term "absorption promoter" is used herein interchangeably with the term "uptake promoter" which refers to a compound capable of enhancing manganese transport across the membranes of the gastrointestinal tract. These compounds are well known in the art from e.g. WO 96/05867 and comprise physiologically tolerable reducing compounds containing an α-hydroxy ketone group, a physiologically tolerable acid containing α- and/or β-hydroxy or amino groups, or a salt thereof, and/or vitamin D.

In one embodiment, the compressed solid composition is provided as defined herein, wherein the one or more absorption promotors are selected from the group consisting of: a proteinogenic amino acid and a vitamin D.

In one embodiment, the compressed solid composition is provided as defined herein, wherein the proteinogenic amino acid is selected from the group consisting of alanine, valine, leucine, tryptophan, methionine, isoleucine, proline, phenylalanine, serine, glycine, threonine, cysteine, asparagine, glutamine, tyrosine, aspartic acid, glutamic acid, arginine, lysine and histidine.

In one embodiment, the compressed solid composition is provided as defined herein, wherein the proteinogenic amino acid is a neutral amino acid.

In one embodiment, the compressed solid composition is provided as defined herein, wherein the proteinogenic amino acid is L-alanine.

In one embodiment, the compressed solid composition is provided as defined herein, wherein the vitamin D is vitamin $D_3$.

In one embodiment, the compressed solid composition is provided as defined herein, comprising two absorptions promoters. In one embodiment, the two absorption promoters are L-alanine and vitamin $D_3$.

In one embodiment, the compressed solid composition is provided as defined herein, wherein the compressed solid composition comprises between 0.25 g and 0.75 g of a proteinogenic amino acid, such as L-alanine, such as between 0.30 g and 0.70 g, such as between 0.35 g and 0.65 g, such as between 0.40 g and 0.60 g, such as between 0.45 g and 0.55 g, such as 0.50 g.

Effervescent Compositions

In one embodiment, the compressed solid composition as provided herein is in the form of an effervescent solid composition, such as an effervescent tablet. An effervescent composition as disclosed herein comprises an effervescent couple.

The term "effervescent couple" as used herein refers to a pair of pharmaceutically acceptable excipients, one of which is a basic ingredient and the other is an acidic ingredient. The basic ingredient liberates carbon dioxide when it comes in contact with the acidic ingredient and water. An example of the basic ingredient is bicarbonate also known as hydrogen carbonate.

In one embodiment, the acidic ingredient is citric acid, such as citric acid anhydrate. In one embodiment, the acidic ingredient is malic acid.

In one embodiment, the basic ingredient of the effervescent couple is selected from sodium hydrogen carbonate, sodium carbonate anhydrous and a mixture thereof.

In one embodiment, the basic ingredient is sodium bicarbonate and the acidic ingredient is citric acid, such as citric acid anhydride.

In one embodiment, the effervescent tablet has a mass of between 1.8 g and 4.0 g, such as between 1.9 g and 3.9 g, such as between 2.0 g and 3.8 g, such as between 2.1 g and 3.7 g, such as between 2.2 g and 3.6 g, such as between 2.3 g and 3.5 g.

In one embodiment, the compressed solid composition has a mass of between 1.8 g and 8.0 g, such as between 1.9 g and 6.0 g, such as between 2.0 g and 4.0 g.

In one embodiment, the effervescent tablet comprises manganese (II) chloride dihydrate.

In one embodiment, the compressed solid composition is provided as an effervescent tablet comprising bicarbonate, such as granulated bicarbonate.

In one embodiment, the effervescent tablet comprises citric acid, such as anhydrous citric acid or citric acid monohydrate.

In one embodiment, the compressed solid composition is provided as defined herein, wherein the mass ratio between citric acid and sodium bicarbonate in the effervescent tablet is at least 1.2 to 1, such as at least 1.3 to 1, such as at least 1.4 to 1, such as at least 1.5 to 1, such as at least 1.6 to 1, such as at least 1.7 to 1, such as at least 1.8 to 1, such as at least 1.9 to 1, such as at least 1.9 to 1, such as at least 2.0 to 1, such as at least 2.1 to 1, such as at least 2.2 to 1, such as at least 2.3 to 1, such as at least 2.4 to 1, such as at least 2.5 to 1.

In one embodiment, the effervescent tablet comprises a sweetener, such as isomalt, which is optionally granulated isomalt. Isomalt is mainly used as a filler in the context of the present disclosure.

In one embodiment, the effervescent tablet is configured such that, after being dispensed into water, the effervescence period terminates at the time where dissolution of the compression solid composition is complete. Hence, the termination of effervescence may provide an indication of when the oral solution is ready to use.

In one embodiment, the compressed solid composition is provided as an effervescent tablet comprising:
 a) Manganese chloride tetrahydrate or dihydrate;
 b) Alanine, such as L-alanine;
 c) Isomalt;
 d) Bicarbonate, such as sodium bicarbonate;
 e) Citric acid, such as citric acid monohydrate; and
 f) Polyethylene glycol, such as polyethylene glycol 6000 (PEG6000).

In one embodiment, the effervescent tablet further comprises vitamin D, such as vitamin $D_3$.

In one embodiment, the effervescent tablet is prepared from a granulate, such as a sodium bicarbonate granulate.

In one embodiment, the granulate comprises sodium bicarbonate, isomalt, and povidone. In one embodiment, the granulate comprises by mass 68.7% sodium bicarbonate, 26.7% isomalt, and 4.6% povidone.

In a preferred embodiment, the mass of the effervescent tablet is about 2.5 g, such as 2.44 g.

In one embodiment, the effervescent tablet comprises:

| Effervescent tablet composition | (%) | (mg) |
|---|---|---|
| Manganese chloride dihydrate* | 26.82 | 654.41 |
| L-alanine | 20.5 | 500.20 |
| Dry vitamin D3 powder, 100 000 IU | 0.39 | 9.52 |
| Sodium bicarbonate granulate | 15.09 | 368.20 |
| Citric acid anhydrate | 24.61 | 600.48 |
| Isomalt | 6.68 | 162.99 |
| PEG6000 | 5.96 | 145.42 |
| Total (in gram) | | 2.44 |

*654.41 mg of manganese chloride dihydrate is equimolar to 800 mg of manganese chloride tetrahydrate.

In a preferred embodiment, the effervescent tablet comprises:

| Tablet composition | (%) | (mg) |
|---|---|---|
| Manganese chloride dihydrate* | 26.82 | 654.41 |
| L-alanine | 20.5 | 500.20 |
| Dry vitamin D3 powder, 100 000 IU | 0.39 | 9.52 |
| Sodium bicarbonate | 10.37 | 252.95 |
| Povidone | 0.69 | 16.94 |
| Citric acid anhydrate | 24.61 | 600.48 |
| Isomalt | 10.71 | 261.30 |
| PEG6000 | 5.96 | 145.42 |
| Total (in gram) | | 2.44 |

*654.41 mg of manganese chloride dihydrate is equimolar to 800 mg of manganese chloride tetrahydrate.

In one embodiment, the composition of vitamin D3 powder 100 000 IU is:

| Component | Quantity in mg/g |
|---|---|
| Sucrose | 175 mg |
| Sodium Ascorbate Crystalline | 40 mg |
| Vitamin D$_3$ Crystalline | 2.5 mg |
| Medium Chain Triglycerides | 30 mg |
| Silicon Dioxide | 12 mg |
| DL-alpha-Tocopherol | 10 mg |
| Modified Food Starch | 730.5 mg |

In one embodiment, the effervescent tablet comprises from 480-1120 IU Vitamin D3.

Packaging

The compressed solid composition as defined herein is preferably packaged using a water-proof or moisture-tight material, such as a blister pack of a suitable water-proof or moisture-tight material known to the skilled person, optionally made of aluminium. Blister packs are pre-formed packaging used for solid compositions, such as the compressed solid composition provided herein. Blister packs are useful for protecting drugs against external factors, such as humidity and contamination for extended periods of time.

In one embodiment, a kit of parts is provided comprising; a compressed solid composition as defined herein, and a water-proof packaging that protects the compressed solid composition from moisture.

Preparation of the Compressed Solid Composition

In one embodiment, a method for preparing the compressed solid composition as defined herein is provided, wherein the method comprises the steps of:
 a) Providing a physiologically acceptable manganese (II) compound, optionally as a granulate, and optionally drying the physiologically acceptable manganese (II) compound;
 b) providing one or more water-soluble excipients allowing for compression;
 c) Mixing the physiologically acceptable manganese (II) compound with one or more absorption promoters and the one or more water-soluble excipients to provide a water-soluble mixture; and
 d) Compressing the water-soluble mixture to provide a compressed solid composition as defined herein.

In one embodiment, the method as defined herein is provided, wherein the relative humidity (rH) is kept below 35%, such as below 34%, such as below 33%, such as below 32%, such as below 31%, such as below 30%, such as below 29%, such as below 28%, such as below 27%, such as below 26%, such as below 25%, such as below 24%, such as below 23%, such as below 22%, such as below 21%, such as below 20%, such as below 19%, such as below 18%, such as below 17%, such as below 16%, such as below 15%, such as below 14%, such as below 13%, such as below 12%, such as below 11%, such as below 10%.

In one embodiment the relative humidity (rH) is kept below 30%.

In one embodiment the relative humidity (rH) is kept below 25%.

In one embodiment the relative humidity (rH) is kept below 20%.

In one embodiment, a compressed solid composition is provided as prepared by the method defined herein.

Items

I-1. A compressed solid composition comprising: a physiologically acceptable manganese (II) compound, one or more absorption promoters, and one or more water-soluble excipients.

I-2. The compressed solid composition according to item 1 for use in preparing an oral solution.

I-3. The compressed solid composition for use as a magnetic resonance imaging (MRI) contrast composition.

I-4. The compressed solid composition according to any one of the preceding items, wherein the one or more water-soluble excipients are non-hygroscopic water-soluble excipients.

I-5. The compressed solid composition according to any one of the preceding items, wherein the one or more water-soluble excipients are selected from the group consisting of: a non-hygroscopic filler, a non-hygroscopic binder, a non-hygroscopic disintegrant, and a non-hygroscopic lubricant.

I-6. The compressed solid composition according to any one of the preceding items, wherein the non-hygroscopic filler is selected from the group consisting of: isomalt; lactose, such as spray-dried lactose, α-lactose, or β-lactose; maltitol; maltose; and mannitol.

I-7. The compressed solid composition according to any one of the preceding items, wherein the compressed solid composition does not comprise a hygroscopic filler selected from the group consisting of: a dextrate, dextrose, fructose, hypromellose, maltodextrin, sucrose, sorbitol and xylitol.

I-8. The compressed solid composition according to any one of the preceding items, wherein the compressed solid composition does not comprise a water-insoluble filler selected from the group consisting of: calcium carbonate; calcium phosphate, such as basic calcium phosphate, calcium hydrogen phosphate, or dicalcium phosphate; calcium silicate; cellulose powder; cellulose acetate; magnesium carbonate; magnesium oxide; a medium-chain triglyceride; microcrystalline cellulose; silicified microcrystalline cellulose; a polymethacrylate; starch; calcium sulfate; and pregelatinized starch.

I-9. The compressed solid composition according to any one of the preceding items, wherein the non-hygroscopic binder is selected from the group consisting of: hydroxyethylmethyl cellulose, maltose, povidone, and dextrin.

I-10. The compressed solid composition according to any one of the preceding items, wherein the compressed solid composition does not comprise a poorly water-soluble binder selected from the group consisting of: acacia, hypromellose, methylcellulose, sodium alginate, pre-gelatinized starch, inulin, agar, gelatin, starch, alginic acid, cellulose acetate phthalate, ethylcellulose, hydrogenated vegetable oil, magnesium aluminum silicate, microcrystalline cellulose, and polymethacrylate.

I-11. The compressed solid composition according to any one of the preceding items, wherein the non-hygroscopic disintegrant is povidone.

I-12. The compressed solid composition according to any one of the preceding items, further comprising a water-insoluble disintegrant.

I-13. The compressed solid composition according to any one of the preceding items, wherein the water-insoluble disintegrant is selected from the group consisting of: carboxymethylcellulose calcium; croscarmellose sodium; and crospovidone.

I-14. The compressed solid composition according to any one of the preceding items, wherein the compressed solid composition does not comprise a hygroscopic disintegrant selected from the group consisting of: carboxymethylcellulose sodium and hydroxypropyl cellulose.

I-15. The compressed solid composition according to any one of the preceding items, wherein the non-hygroscopic lubricant is selected from the group consisting of: polyethylene glycol 6000 and sodium benzoate.

I-16. The compressed solid composition according to any one of the preceding items, wherein the compressed solid composition does not comprise a hygroscopic lubricant selected from the group consisting of: poloxamer and polyethylene glycol 4000.

I-17. The compressed solid composition according to any one of the preceding items, wherein the compressed solid composition does not comprise a water-insoluble lubricant selected from the group consisting of: sodium stearyl fumarate, calcium stearate, colloidal silica, glycerin monostearate, glyceryl behenate, glyceryl palmitostearate, hydrogenated castor oil, hydrogenated vegetable oil, magnesium stearate, medium-chain triglycerides, palmitic acid, stearic acid, talc, and zinc stearate.

I-18. The compressed solid composition according to any one of the preceding items, wherein the physiologically acceptable manganese (II) compound is a salt of an inorganic anion or an organic anion.

I-19. The compressed solid composition according to any one of the preceding items, wherein the inorganic anion is selected from the group consisting of chloride, fluoride, bromide, iodide, sulphate, and phosphate.

I-20. The compressed solid composition according to any one of the preceding items, wherein the organic anion is selected from the group consisting of: ascorbate, kojate, salicylate, and gluconate.

I-21. The compressed solid composition according to any one of the preceding items, wherein the physiologically acceptable manganese (II) compound is selected from the group consisting of: manganese (II) sulphate, manganese (II) gluconate, manganese (II) chloride anhydrate, manganese (II) chloride dihydrate, manganese (II) chloride tetrahydrate, and a combination thereof.

I-22. The compressed solid composition according to any one of the preceding items, wherein the physiologically acceptable manganese (II) compound is manganese (II) chloride tetrahydrate.

I-23. The compressed solid composition according to any one of the preceding items, wherein the one or more absorption promotors are selected from the group consisting of: a proteinogenic amino acid and a vitamin D.

I-24. The compressed solid composition according to any one of the preceding items, wherein the proteinogenic amino acid is selected from the group consisting of alanine, valine, leucine, tryptophan, methionine, isoleucine, proline, phenylalanine, serine, glycine, threonine, cysteine, asparagine, glutamine, tyrosine, aspartic acid, glutamic acid, arginine, lysine and histidine.

I-25. The compressed solid composition according to any one of the preceding items, wherein the proteinogenic amino acid is a neutral amino acid.

I-26. The compressed solid composition according to any one of the preceding items, wherein the proteinogenic amino acid is L-alanine.

I-27. The compressed solid composition according to any one of the preceding items, wherein the vitamin D is vitamin $D_3$.

I-28. The compressed solid composition according to any one of the preceding items, comprising two absorptions promoters.

I-29. The compressed solid composition according to any one of the preceding items, wherein the two absorption promoters are L-alanine and vitamin $D_3$.

I-30. The compressed solid composition according to any one of the preceding items, wherein the compressed solid composition comprises between 0.5 g and 1.2 g manganese (II) chloride tetrahydrate or an equimolar amount of any corresponding manganese (II) salt.

I-31. The compressed solid composition according to any one of the preceding items, wherein the compressed solid composition comprises between 0.6 g and 1 g of manganese (II) chloride tetrahydrate, such as between 0.65 g and 0.95 g, such as between 0.70 g and 0.90 g, such as between 0.75 g and 0.85 g, such as 0.80 g.

I-32. The compressed solid composition according to any one of the preceding items, wherein the compressed solid composition comprises 0.8 g manganese (II) chloride tetrahydrate or an equimolar amount of any corresponding manganese (II) salt.

I-33. The compressed solid composition according to any one of the preceding items, wherein the compressed solid composition comprises 0.8 g manganese (II)

chloride tetrahydrate or an equimolar amount of the corresponding anhydrate or dihydrate.

I-34. The compressed solid composition according to any one of the preceding items, wherein the compressed solid composition comprises between 0.25 g and 0.75 g of L-alanine, such as between 0.30 g and 0.70 g, such as between 0.35 g and 0.65 g, such as between 0.40 g and 0.60 g, such as between 0.45 g and 0.55 g, such as 0.50 g.

I-35. The compressed solid composition according to any one of the preceding items, wherein the compressed solid composition provides a clear solution in water at room temperature within 8 minutes or less, such as within 7 minutes or less, such as within 6 minutes or less, such as within 5 minutes or less, such as within 4 minutes or less, such as within 3 minutes or less, without stirring or agitation of the solution.

I-36. The compressed solid composition according to any one of the preceding items, wherein the compressed solid composition provides a clear solution in 0.2 L water at room temperature within 8 minutes or less, such as within 7 minutes or less, such as within 6 minutes or less, such as within 5 minutes or less, such as within 4 minutes or less, such as within 3 minutes or less, without stirring or agitation of the solution.

I-37. The compressed solid composition according to any one of the preceding items, wherein the compressed solid composition completely dissolves in water at room temperature within 8 minutes or less, such as within 7 minutes or less, such as within 6 minutes or less, such as within 5 minutes or less, such as within 4 minutes or less, such as within 3 minutes or less, without stirring or agitation of the solution.

I-38. The compressed solid composition according to any one of the preceding items, wherein the compressed solid composition disintegrates within less than 3.0 minutes in water at room temperature, such as within less than 2.5 minutes, such as within less than 2 minutes, such as within less than 1.5 minutes, such as within less than 1 minute, without any stirring or agitation of the solution.

I-39. The compressed solid composition according to any one of the preceding items, wherein the compressed solid composition disintegrates within less than 3.0 minutes in 0.2 L water at room temperature, such as within less than 2.5 minutes, such as within less than 2 minutes, such as within less than 1.5 minutes, such as within less than 1 minute, without any stirring or agitation of the solution.

I-40. The compressed solid composition according to any one of the preceding items, wherein the compressed solid composition results in a pH of between 2 to 7 in 0.2 L water after complete dissolution of between 0.5 g and 1 g manganese (II) chloride tetrahydrate or an equimolar amount of any corresponding manganese (II) salt.

I-41. The compressed solid composition according to any one of the preceding items, wherein the compressed solid composition is an effervescent composition.

I-42. The compressed solid composition according to any one of the preceding items, wherein the effervescent tablet has a mass of between 1.8 g and 4.0 g, such as between 1.9 g and 3.9 g, such as between 2.0 g and 3.8 g, such as between 2.1 g and 3.7 g, such as between 2.2 g and 3.6 g, such as between 2.3 g and 3.5 g.

I-43. The compressed solid composition according to any one of the preceding items, wherein the effervescent tablet comprises manganese (II) chloride dihydrate.

I-44. The compressed solid composition according to any one of the preceding items, wherein the effervescent tablet comprises bicarbonate, such as granulated bicarbonate.

I-45. The compressed solid composition according to any one of the preceding items, wherein the effervescent tablet comprises citric acid, such as anhydrous citric acid or citric acid monohydrate.

I-46. The compressed solid composition according to any one of the preceding items, wherein the mass ratio between citric acid and sodium bicarbonate in the effervescent tablet is at least 1.2 to 1, such as at least 1.3 to 1, such as at least 1.4 to 1, such as at least 1.5 to 1, such as at least 1.6 to 1, such as at least 1.7 to 1, such as at least 1.8 to 1, such as at least 1.9 to 1, such as at least 1.9 to 1, such as at least 2.0 to 1, such as at least 2.1 to 1, such as at least 2.2 to 1, such as at least 2.3 to 1, such as at least 2.4 to 1, such as at least 2.5 to 1.

I-47. The compressed solid composition according to any one of the preceding items, wherein the effervescent tablet comprises:
 a. Manganese chloride tetrahydrate, dihydrate, or anhydrate;
 b. Alanine;
 c. Isomalt;
 d. Bicarbonate, such as sodium bicarbonate;
 e. Citric acid, such as citric acid monohydrate; and
 f. Polyethylene glycol, such as polyethylene glycol 6000 (PEG6000).

I-48. The compressed solid composition according to item 47, further comprising vitamin $D_3$.

I-49. The compressed solid composition according to any one of the preceding items, wherein the composition comprises:
 a. Manganese (II) chloride tetrahydrate, dihydrate, or anhydrate;
 b. Alanine;
 c. Isomalt;
 d. Croscarmellose, such as croscarmellose sodium; and
 e. Polyethylene glycol, such as PEG6000.

I-50. The compressed solid composition according to item 49, further comprising vitamin $D_3$.

I-51. A kit of parts comprising;
 a) a compressed solid composition as defined in any one of the preceding items; and
 b) a water-proof packaging.

I-52. A method for preparing the compressed solid composition as defined in any one of the preceding items, wherein the method comprises the steps of:
 a. providing a physiologically acceptable manganese (II) compound, optionally as a granulate, and optionally drying the physiologically acceptable manganese (II) compound;
 b. providing one or more absorption promoters;
 c. providing one or more water-soluble excipients allowing for compression;
 d. mixing the physiologically acceptable manganese (II) compound with the one or more absorption promoters and the one or more water-soluble excipients to provide a water-soluble mixture; and
 e. compressing the water-soluble mixture to provide a compressed solid composition as defined in any one of the preceding items.

I-53. The method according to any one of the preceding items, wherein the relative humidity (RH) is kept below 35%, such as below 34%, such as below 33%, such as below 32%, such as below 31%, such as below 30%, such as below 29%, such as below 28%, such as below 27%, such as below 26%, such as below 25%, such as below 24%, such as below 23%, such as below 22%, such as below 21%, such as below 20%, such as below 19%, such as below 18%, such as below 17%, such as below 16%, such as below 15%, such as below 14%, such as below 13%, such as below 12%, such as below 11%, such as below 10%.

I-54. A compressed solid composition prepared by the method according to any one of the preceding items.

I-55. A method for preparing an oral MRI solution comprising:
  a. providing a compressed solid composition as defined in any one of the preceding items,
  b. providing a suitable amount of water, and
  c. adding said compressed solid composition to said water, thereby forming the oral MRI solution.

Items II

1. A compressed solid composition comprising: a physiologically acceptable manganese (II) compound, one or more absorption promoters, and one or more water-soluble excipients, optionally wherein the compressed solid composition is for preparing an oral solution, such as for use in magnetic resonance imaging (MRI).
2. The compressed solid composition according to item 1, wherein the one or more water-soluble excipients are selected from the group consisting of: a non-hygroscopic filler, a non-hygroscopic binder, a non-hygroscopic disintegrant, and a non-hygroscopic lubricant.
3. The compressed solid composition according to any one of the preceding items, wherein the non-hygroscopic filler is selected from the group consisting of: isomalt; lactose, such as spray-dried lactose, α-lactose, or β-lactose; maltitol; maltose; and mannitol.
4. The compressed solid composition according to any one of the preceding items, wherein the non-hygroscopic binder is selected from the group consisting of: hydroxyethylmethyl cellulose, maltose, povidone, and dextrin.
5. The compressed solid composition according to any one of the preceding items, wherein the non-hygroscopic disintegrant is povidone.
6. The compressed solid composition according to any one of the preceding items, wherein the non-hygroscopic lubricant is selected from the group consisting of: polyethylene glycol 6000 and sodium benzoate.
7. The compressed solid composition according to any one of the preceding items, wherein the physiologically acceptable manganese (II) compound is selected from the group consisting of: manganese (II) sulphate, manganese (II) gluconate, manganese (II) chloride anhydrate, manganese (II) chloride dihydrate, manganese (II) chloride tetrahydrate, and a combination thereof.
8. The compressed solid composition according to any one of the preceding items, wherein the one or more absorption promotors are selected from the group consisting of: a proteinogenic amino acid and a vitamin D, optionally wherein the compressed solid composition comprises two absorption promoters, such as L-alanine and vitamin $D_3$.
9. The compressed solid composition according to any one of the preceding items, wherein the compressed solid composition comprises between 0.5 g and 1.2 g manganese (II) chloride tetrahydrate or an equimolar amount of any corresponding manganese (II) salt.
10. The compressed solid composition according to any one of the preceding items, wherein the compressed solid composition provides a clear solution and/or completely dissolves in water, such as 0.2 L, at room temperature within 8 minutes or less, such as within 7 minutes or less, such as within 6 minutes or less, such as within 5 minutes or less, such as within 4 minutes or less, such as within 3 minutes or less, without stirring or agitation of the solution.
11. The compressed solid composition according to any one of the preceding items, wherein the compressed solid composition results in a pH of between 2 to 7 in 0.2 L water after complete dissolution of between 0.5 g and 1 g manganese (II) chloride tetrahydrate or an equimolar amount of any corresponding manganese (II) salt.
12. The compressed solid composition according to any one of the preceding items, wherein the compressed solid composition is an effervescent composition.
13. A method for preparing the compressed solid composition as defined in any one of the preceding items, wherein the method comprises the steps of:
  a. providing a physiologically acceptable manganese (II) compound, optionally as a granulate, and optionally drying the physiologically acceptable manganese (II) compound;
  b. providing one or more absorption promoters;
  c. providing one or more water-soluble excipients allowing for compression;
  d. mixing the physiologically acceptable manganese (II) compound with the one or more absorption promoters and the one or more water-soluble excipients to provide a water-soluble mixture; and
  e. compressing the water-soluble mixture to provide a compressed solid composition as defined in any one of the preceding items.
14. The method according to any one of the preceding items, wherein the relative humidity (RH) is kept below 35%, such as below 34%, such as below 33%, such as below 32%, such as below 31%, such as below 30%, such as below 29%, such as below 28%, such as below 27%, such as below 26%, such as below 25%, such as below 24%, such as below 23%, such as below 22%, such as below 21%, such as below 20%, such as below 19%, such as below 18%, such as below 17%, such as below 16%, such as below 15%, such as below 14%, such as below 13%, such as below 12%, such as below 11%, such as below 10%.
15. A method for preparing an oral MRI solution comprising:
  a. providing a compressed solid composition as defined in any one of the preceding items,
  b. providing a suitable amount of water, and
  c. adding said compressed solid composition to said water, thereby forming the oral MRI solution.

Items III

1. An effervescent MRI tablet for magnetic resonance imaging (MRI) comprising:
  a) in the range of 0.50 g to 1.2 g manganese (II) chloride tetrahydrate or an equimolar amount of the corresponding anhydrate or dihydrate;
  b) in the range of 0.25 g to 0.75 g of L-alanine;
  c) one or more water-soluble excipients; and d) an effervescent couple comprising a basic ingredient and an acidic ingredient; wherein the effervescent tablet is for preparing an oral solution for use in MRI.

2. The effervescent MRI tablet according to item 1, wherein the one or more water-soluble excipients are selected from the group consisting of: a non-hygroscopic filler, a non-hygroscopic binder, a non-hygroscopic disintegrant, a non-hygroscopic lubricant, and combinations thereof.

3. The effervescent MRI tablet according to item 2 comprising the non-hygroscopic filler, wherein the non-hygroscopic filler is selected from the group consisting of: isomalt; lactose; maltitol; maltose; and mannitol.

4. The effervescent MRI tablet according to item 2 comprising the non-hygroscopic binder, wherein the non-hygroscopic binder is selected from the group consisting of: hydroxyethylmethyl cellulose; maltose; povidone; and dextrin.

5. The effervescent MRI tablet according to item 2 comprising the non-hygroscopic disintegrant povidone.

6. The effervescent MRI tablet according to item 2 comprising the non-hygroscopic lubricant, wherein the non-hygroscopic lubricant is selected from the group consisting of: polyethylene glycol 6000; and sodium benzoate.

7. The effervescent MRI tablet according to item 1, wherein the effervescent MRI tablet further comprises vitamin $D_3$.

8. The effervescent MRI tablet according to item 1, wherein the effervescent MRI tablet comprises 0.50 g L-alanine.

9. The effervescent MRI tablet according to item 1, wherein the effervescent MRI tablet provides a clear solution in 0.2 L water at room temperature within 5 minutes or less without stirring or agitation of the solution.

10. The effervescent MRI tablet according to item 1, wherein the effervescent MRI tablet completely dissolves in water at room temperature within 5 minutes or less without stirring or agitation of the solution.

11. The effervescent MRI tablet according to item 1, wherein the effervescent MRI tablet disintegrates within less than 3.0 minutes in 0.2 L water at room temperature without any stirring or agitation of the solution.

12. The effervescent MRI tablet according to item 1, wherein the effervescent MRI tablet results in a pH of between 2 to 7 in 0.2 L water after complete dissolution of between 0.5 g and 1 g manganese (II) chloride tetrahydrate or an equimolar amount of the corresponding anhydrate or dihydrate.

13. The effervescent MRI tablet according to item 1, wherein the effervescent MRI tablet has a mass in the range of 1.8 g to 4.0 g.

14. The effervescent MRI tablet according to item 1, wherein the effervescent MRI tablet comprises granulated bicarbonate.

15. The effervescent MRI tablet according to item 1, wherein the effervescent MRI tablet comprises citric acid.

16. The effervescent MRI tablet according to item 1, comprising citric acid and sodium bicarbonate, wherein a mass ratio between the citric acid and the sodium bicarbonate in the effervescent MRI tablet is 1.2 to 1.

17. The effervescent MRI tablet according to item 1, wherein the effervescent MRI tablet comprises:
  a. Manganese chloride tetrahydrate, dihydrate, or anhydrate;
  b. L-Alanine;
  c. Isomalt;
  d. Sodium bicarbonate;
  e. Citric acid; and
  f. PEG6000.

18. The effervescent MRI tablet according to item 1, wherein the effervescent MRI tablet consists of:
  a. Manganese chloride tetrahydrate, dihydrate, or anhydrate;
  b. L-Alanine;
  c. Isomalt;
  d. Sodium bicarbonate;
  e. Citric acid;
  f. PEG6000;
  g. Povidone; and
  h. Vitamin $D_3$.

19. A method for preparing the effervescent MRI tablet as defined in item 1, wherein the method comprises the steps of:
  a) providing a physiologically acceptable manganese (II) compound;
  b) providing one or more absorption promoters;
  c) providing one or more water-soluble excipients allowing for compression;
  d) mixing the physiologically acceptable manganese (II) compound with the one or more absorption promoters and the one or more water-soluble excipients to provide a water-soluble mixture; and
  e) compressing the water-soluble mixture to provide an effervescent MRI tablet; wherein the relative humidity (RH) is kept below 30%.

20. A method for preparing an oral MRI solution comprising:
  a. providing an effervescent MRI tablet as defined in item 1,
  b. providing a suitable amount of water, and
  c. adding said effervescent MRI tablet to said water,
  d. thereby forming the oral MRI solution.

EXAMPLES

In the following examples, examples 1 to 9 are related to a non-effervescent tablet, herein referred to as "soluble tablet" and examples 10 to 18 are related to an effervescent tablet, herein referred to as "effervescent tablet".

Examples 1-3 are examples of formulations leading to a clear solution within 5 minutes after introduction into water.

Examples 4, and 7-8 demonstrate the issues associated with too high air humidity.

Example 5 demonstrates that drying the Manganese chloride before mixing can lead to issues of high hygroscopicity.

Examples 6 and 9 are examples of compositions that do not result in a clear solution after introduction into water.

Examples 10-12 demonstrate the preparation of effervescent tablets produced under low relative humidity that perform well.

Examples 13-14 demonstrate how effervescent tablets, prepared under higher relative humidity, do not perform well.

Examples 11 and 15-18 demonstrate the effects of drying manganese chloride directly or during a granulation process.

Examples 16-18 demonstrate the effect of granulating a tablet ingredient to adjust the dissolution profile.

Example 1: Soluble Tablet Based on Isomalt with Tablet Weight 2000 mg

Manganese chloride tetrahydrate, Alanine, Isomalt, Croscarmellose sodium and PEG6000 were mixed for 5 minutes where the relative humidity (rH) in the air was 24% rH. Tablets were compressed on a single punch tablet press using 20 mm flat faced tooling with a tablet weight of 2000 mg and a hardness of 40N. Content of Manganese chloride tetrahydrate was 800 mg/tablet and content of Alanine was 500 mg/tablet. One tablet was put into a glass with 200 ml water at room temperature, and the tablet disintegrated within one minute and was totally dissolved quickly within three minutes giving a clear solution.

Conclusion

At low relative humidity in the air, tablets can be produced according to the method above and will quickly disintegrate and dissolve forming a clear solution with neutral taste.

Example 2: Soluble Tablet Based on Isomalt with Tablet Weight 2500 mg

Manganese chloride tetrahydrate, Alanine, Isomalt, Croscarmellose sodium and PEG6000 were mixed for 5 minutes. Tablets were compressed on a single punch tablet press using 20 mm flat faced tooling with a tablet weight of 2500 mg and a hardness of 90N. Content of Manganese chloride tetrahydrate was 800 mg/tablet and content of Alanine was 500 mg/tablet. One tablet was put into a glass with 200 ml water at room temperature, and the tablet disintegrated within three minute and was totally dissolved within five minutes giving a clear solution.

Example 3: Soluble Tablet Based on Isomalt with Tablet Weight 2000 mg Added Vitamin D Manganese chloride tetrahydrate, Alanine, Dry Vitamin $D_3$ 100 SD/S, Isomalt, Croscarmellose sodium and PEG6000 were mixed for 5 minutes. Tablets were compressed on a single punch tablet press using 20 mm flat faced tooling with a tablet weight of 2000 mg. Content of Manganese chloride tetrahydrate was 800 mg/tablet, content of Alanine was 500 mg/tablet and content of Vitamin D was 20 µg/tablet plus 20% overage. One tablet was put into a glass with 200 ml water at room temperature, and the tablet was totally dissolved within five minutes giving a clear solution with a little shadow from Vitamin D on top.

Example 4: Soluble Tablet Based on Isomalt with Tablet Weight 2000 mg Added Vitamin D Adsorbs Moisture at 35% rH Manganese chloride tetrahydrate, Alanine, Dry Vitamin D3 100 SD/S, Isomalt, Croscarmellose sodium and PEG6000 were mixed for 5 minutes where the relative humidity in the air was 35% rH. Tablets were compressed on a single punch tablet press using 20 mm flat faced tooling with a tablet weight of 2000 mg and a hardness of 85N. During processing, the granulate adsorbed moisture from the air, formed lumps and dosed badly on the tablet press. Content of Manganese chloride tetrahydrate was 800 mg/tablet, content of Alanine was 500 mg/tablet and content of Vitamin D was 20 µg/tablet plus 20% overage. One tablet was put into a glass with 200 ml water at room temperature, and the tablet disintegrated within four minutes and was totally dissolved within nine minutes giving a clear solution.

Conclusion

The humidity in the air of the production area needs to be kept low, such as below 25% rH, otherwise the mix will adsorb moisture and form lumps as well as the time for tablet dissolution will increase.

Example 5: Soluble Tablet Based on Isomalt where Manganese Chloride was Dried Manganese chloride tetrahydrate was dried at 100° C. overnight until constant weight. About 22% of the weight was lost. The dried Manganese chloride, Alanine, Dry Vitamin $D_3$ 100 SD/S, Isomalt, Croscarmellose sodium and PEG6000 were mixed for 5 minutes where the relative humidity in the air was 17% rH. Tablets were compressed on a single punch tablet press using 20 mm flat faced tooling with a tablet weight of 2000 mg and a hardness of 61N. Content of Manganese chloride tetrahydrate was 800 mg/tablet, content of Alanine was 500 mg/tablet and content of Vitamin D was 20 µg/tablet plus 20% overage. One tablet was put into a glass with 200 ml water at room temperature, and the tablet did not disintegrate but dissolved slowly from the surface. The tablet was totally dissolved within eight minutes giving a clear solution with a little shadow from Vitamin D on top.

Conclusion

This example demonstrates that drying manganese chloride tetrahydrate made it very hygroscopic and it took up the moisture from the disintegrant, which lost its effect. The tablet was however still able to dissolve to give a clear solution apart from the oily vitamin $D_3$ in the top.

TABLE 1

| Batch compositions for Example 1 to 5 in gram. | | | | | |
|---|---|---|---|---|---|
|  | Example 1 | Example 2 | Example 3 | Example 4 | Example 5 |
| Manganese chloride tetrahydrate | 20.0 | 20.0 | 16.0 | 208.00 | — |
| Manganese chloride tetrahydrate, dried | — | — | — | — | 13.1 |
| Alanine | 12.5 | 12.5 | 10.5 | 130.00 | 10.0 |
| Dry Vitamin $D_3$ 100 SD/S | — | — | 9.6 | 2.50 | 0.19 |

TABLE 1-continued

Batch compositions for Example 1 to 5 in gram.

|  | Example 1 | Example 2 | Example 3 | Example 4 | Example 5 |
|---|---|---|---|---|---|
| Isomalt | 14.25 | 23.44 | 10.61 | 137.90 | 13.52 |
| Croscarmellose sodium | 0.25 | 0.31 | 0.8 | 10.40 | 0.8 |
| PEG6000 | 3.0 | 6.25 | 2.4 | 31.20 | 2.4 |
| Total | 50.0 | 62.5 | 40.0 | 520.0 | 40.0 |

Example 6: Soluble Tablet Based on Isomalt with Tablet Weight 2000 mg but with Water-Insoluble Disintegrant Manganese chloride tetrahydrate, Alanine, Isomalt, Crospovidone and PEG6000 were mixed for 5 minutes where the relative humidity in the air was 24% rH. Tablets were compressed on a single punch tablet press using 20 mm flat faced tooling with a tablet weight of 2000 mg and a hardness of 40N. Content of Manganese chloride tetrahydrate was 800 mg/tablet and content of Alanine was 500 mg/tablet. One tablet was put into a glass with 200 ml water at room temperature, and the tablet disintegrated within one minute and was totally dissolved quickly within three minutes giving a clear solution with particles of crospovidone not dissolved.

Conclusion

Based on this example, it appears that the use of a water-insoluble disintegrant, such as crospovidone, does not provide a clear solution even at low levels of disintegrant.

Example 7: Soluble Tablet Based on Mannitol at High Humidity

Manganese chloride tetrahydrate, Alanine, Mannitol, Crospovidone and PEG6000 were mixed for 5 minutes where the relative humidity in the air was 45% rH. Tablets were compressed on a single punch tablet press using 12 mm flat faced tooling with a tablet weight of 666. During processing, the granulate adsorbed moisture from the air, resulting in severe sticking to the punch and die. Content of Manganese chloride tetrahydrate was 800 mg/3 tablets and content of Alanine was 500 mg/3 tablets. Three tablets were put into a glass with 200 ml water at room temperature, and the tablets were totally dissolved within five minutes giving a clear solution with a sweet taste.

Conclusion

The humidity in the air of production area needs to be kept low, such as below 25% rH, otherwise the mix will adsorb moisture and form lumps, which will result in an ineffective tableting process and introduce uncertainty with respect to the final dosages in the tablets.

Example 8: Soluble Tablet Based on Maltitol at High Humidity

Manganese chloride tetrahydrate, Alanine, Maltitol, Crospovidone and PEG6000 were mixed for 5 minutes where the relative humidity in the air was 45% rH. Tablets were compressed on a single punch tablet press using 12 mm flat faced tooling with a tablet weight of 666. During processing, the granulate adsorbed moisture from the air, formed lumps and dosed badly on the tablet press. Content of Manganese chloride tetrahydrate was 800 mg/3 tablets and content of Alanine was 500 mg/3 tablets. Three tablet was put into a glass with 200 ml water at room temperature, and the tablets were totally dissolved within seven minutes giving a clear solution with a bitter taste.

Conclusion

The humidity in the air of production area needs to be kept low, such as below 25% rH, to prevent that the mix will adsorb moisture.

TABLE 2

Batch compositions for Example 6 to 9 in gram.

|  | Example 6 | Example 7 | Example 8 | Example 9 |
|---|---|---|---|---|
| Manganese chloride tetrahydrate | 20.0 | 8.0 | 8.0 | 20.0 |
| Alanine | 12.5 | 5.0 | 5.0 | 12.5 |
| Isomalt | 14.25 | — | — | 14.13 |
| Mannitol | — | 6.5 | — | — |
| Maltitol | — | — | 6.5 | — |
| Croscarmellose sodium | — | 0.1 | 0.1 | — |
| Crospovidone | 0.25 | — | — | 0.25 |
| PEG6000 | 3.0 | 0.4 | 0.4 | 3.0 |
| Magnesium Stearate | — | — | — | 0.13 |
| Total | 50.0 | 20.0 | 20.0 | 50.0 |

Example 9: Soluble Tablet Based on Isomalt with Tablet Weight 2000 mg but with Water-Insoluble Lubricant Manganese chloride tetrahydrate, Alanine, Isomalt, Croscarmellose sodium and PEG6000 were mixed for 5 minutes where the relative humidity in the air was 23% rH. Magnesium stearate was added and mixed for 1 minute. Tablets were compressed on a single punch tablet press using 20 mm flat faced tooling with a tablet weight of 2000 mg and a hardness of 88N. Content of Manganese chloride tetrahydrate was 800 mg/tablet and content of Alanine was 500 mg/tablet. One tablet was put into a glass with 200 ml water at room temperature, and the tablet disintegrated within four minutes and was dissolved within seven minutes.

Conclusion

This example demonstrates that a water-insoluble lubricant, such as magnesium stearate, provided a tablet which upon addition to water resulted in an unclear, greyish opalescent solution with foam on top.

Example 10: Effervescent Tablet Comprising low Amounts of Isomalt Performing Well Manganese chloride tetrahydrate, Alanine, Isomalt, Sodium bicarbonate, Citric acid anhydrate and PEG6000 were mixed for 5 minutes where the relative humidity in the air was 24% rH. Tablets were compressed on a single punch tablet press using 20 mm flat faced tooling with a tablet weight of 2565 mg and a hardness of 56N. Content of Manganese chloride tetrahydrate was 800 mg/tablet and content of Alanine was 500 mg/tablet. One tablet was put into a glass with 200 ml water at room temperature, and the tablet effervesced for about 3.5 minutes. As Manganese ions form precipitate with carbonate ions, a precipitate of Manganese carbonate was formed. At acid pH, this precipitate can be re-dissolved, which was achieved after 4.5 minutes giving a clear solution with a slightly acidic taste.

Conclusion

This example demonstrates that at low relative humidity in the air, such as 24% rH, tablets can be produced which will quickly disintegrate and dissolve in water to provide a clear solution with acceptable taste.

Example 11: Effervescent Tablet Comprising more Isomalt Performing Well

Manganese chloride tetrahydrate, Alanine, Isomalt, Sodium bicarbonate, Citric acid anhydrate and PEG6000 were mixed for 5 minutes where the relative humidity in the air was 24% rH. Tablets were compressed on a single punch tablet press using 20 mm flat faced tooling with a tablet weight of 2990 mg and a hardness of 90N. Content of Manganese chloride tetrahydrate was 800 mg/tablet and content of Alanine was 500 mg/tablet. One tablet was put into a glass with 200 ml water at room temperature, and the tablet effervesced for about 3 minutes. A precipitate of Manganese carbonate was formed, and after 5 minutes it re-dissolved giving a clear solution with slightly acidic taste.

Conclusion

This example demonstrates that at low relative humidity in the air, such as 24% rH, tablets can be produced which will quickly disintegrate and dissolve to provide a clear solution with acceptable taste.

Example 12: Effervescent Tablet with Dried Manganese Chloride

Manganese chloride tetrahydrate was dried at 100° C. overnight until constant weight. About 22% of the weight was lost. The dried Manganese chloride tetrahydrate, Alanine, Isomalt, Sodium bicarbonate, Citric acid anhydrate and PEG6000 were mixed for 5 minutes where the relative humidity in the air was 35% rH. Tablets were compressed on a single punch tablet press using 20 mm flat faced tooling with a tablet weight of 2420 mg and a hardness of 55N. Sticking was encountered as the mix adsorbed moisture from the air. Content of Manganese chloride tetrahydrate was 800 mg/tablet and content of Alanine was 500 mg/tablet. One tablet was put into a glass with 200 ml water at room temperature, and the tablet effervesced for about 3 minutes. A precipitate of Manganese carbonate was formed, and after 3.5 minutes is re-dissolved giving a clear solution with slightly acidic taste.

Conclusion

This example demonstrates that drying manganese chloride tetrahydrate made it very hygroscopic. The hygroscopic manganese chloride took up the moisture from the air causing problems during tabletting but the tablet nevertheless still got quickly into solution.

Example 13: Effervescent Tablet with High Level of "Effervescent Mix" at High Humidity Manganese chloride tetrahydrate, Alanine, Sodium bicarbonate, Citric acid anhydrate and PEG6000 were mixed for 5 minutes where the relative humidity in the air was 44% rH. Tablets were compressed on a single punch tablet press using 12 mm flat faced tooling with a tablet weight of approx. 867 mg. During compression, the mix adsorbed moisture and sticking was found after compressing a few tablets. Content of Manganese chloride tetrahydrate was 800 mg/3 tablets and content of Alanine was 500 mg/3 tablets. Three tablets were dispensed into a glass with 200 ml water at room temperature, and the tablets effervesced for about 2 minutes. A precipitate of Manganese carbonate was formed, and after 5 minutes it was re-dissolved giving a clear solution with slightly acidic taste.

Conclusion

This example demonstrates that the relative humidity of the air in the production area must be kept low to ensure an efficient tabletting process. Producing the tablets at 44% rH caused the mixture to absorb moisture and stick during compression.

Example 14: Effervescent Tablet with Low Level of "Effervescent Mix" at High Humidity Manganese chloride tetrahydrate, Alanine, Sodium bicarbonate, Citric acid anhydrate and PEG6000 were mixed for 5 minutes where the relative humidity in the air was 52% rH. Tablets were compressed on a single punch tablet press using 12 mm flat faced tooling with a tablet weight of approx. 692 mg. During compression, the mix adsorbed moisture and severe sticking was encountered. Content of Manganese chloride tetrahydrate was 800 mg/3 tablets and content of Alanine was 500 mg/3 tablets. Three tablets were put into a glass with 200 ml water at room temperature, and the tablet effervesced for about 3 minutes. A precipitate of Manganese carbonate was formed, and after 5 minutes is re-dissolved giving a clear solution with slightly acid taste.

Conclusion

This example demonstrates that the relative humidity of the air in the production area must be kept low to ensure an efficient tabletting process. Producing the tablets at 52% rH caused the mixture to absorb moisture and stick severely during compression.

TABLE 3

Batch compositions for Example 10 to 14 in gram.

| | Example 10 | Example 11 | Example 12 | Example 13 | Example 14 |
|---|---|---|---|---|---|
| Manganese chloride tetrahydrate | 20.0 | 20.0 | — | 8.0 | 8.0 |
| Manganese chloride tetrahydrate, dried | — | — | 16.36 | — | — |
| Alanine | 12.5 | 12.5 | 12.5 | 5.0 | 5.0 |
| Sodium bicarbonate | 9.38 | 9.38 | 9.38 | 5.0 | 2.5 |
| Citric acid anhydrate | 15.0 | 15.0 | 15.0 | 8.0 | 4.0 |
| Isomalt | 3.64 | 13.64 | 3.64 | — | — |
| PEG6000 | 3.63 | 4.25 | 3.63 | 0.6 | 1.25 |
| Total | 64.14 | 74.77 | 60.50 | 26.6 | 20.75 |

Example 15: Effervescent Tablet with Granulation of Manganese Chloride/Citric Acid 28.1 g Manganese chloride tetrahydrate, 21.1 g Citric acid monohydrate and 0.9 g Povidone were mixed in a high shear mixer. Ethanol 96% was added as granulation aid while stirring until the powder had been adequate wetted (5.3 g). The granulate was dried at 100° C. overnight until constant weight, and sieved through screen 710 µm. Manganese chloride/citric acid granulate, Alanine, Isomalt, Sodium bicarbonate and PEG6000 were mixed for 5 minutes where the relative humidity in the air was 24% rH. Tablets were compressed on a single punch tablet press using 20 mm flat faced tooling with a tablet weight of 2395 mg and a hardness of 70N. Content of Manganese chloride tetrahydrate was 800 mg/tablet, content of Alanine was 500 mg/tablet and content of Citric acid anhydrate was 600 mg/tablet. One tablet was put into a glass with 200 ml water at room temperature, and the tablet effervesced for about 3 minutes. A precipitate of Manganese carbonate was formed (less than previous examples), and after 4 minutes it was re-dissolved giving a clear solution with slightly acid taste.

Conclusion

This example demonstrates that granulating of manganese chloride/citric acid can be beneficial as it lowers the amount of precipitate formed and provides for quick dissolution time of the tablet.

Example 16: Effervescent Tablet with Granulation of Sodium Bicarbonate

Manganese chloride tetrahydrate was dried at 100° C. overnight until constant weight. About 22% of the weight was lost. 68.74 g Sodium bicarbonate, 26.7 g Isomalt and 4.58 g Povidone were mixed in a high shear mixer. Ethanol 96% was added as granulation aid while stirring until the powder had been adequate wetted (19.7 g). The granulate was dried at 100° C. overnight and sieved through screen 710 µm. Dried Manganese chloride tetrahydrate, Alanine, Sodium bicarbonate granulate, Citric acid anhydrate and PEG6000 were mixed for 5 minutes where the relative humidity in the air was 24% rH. Tablets were compressed on a single punch tablet press using 20 mm flat faced tooling with a tablet weight of 2445 mg and a hardness of 68N. Content of Manganese chloride tetrahydrate was 800 mg/tablet, content of Alanine was 500 mg/tablet and content of Sodium bicarbonate was 375 mg/tablet. One tablet was put into a glass with 200 ml water at room temperature, and the tablet effervesced for about 2.5 minutes. A little precipitate of Manganese carbonate was formed (less than previous examples), and after 3.5 minutes it was re-dissolved giving a clear solution with slightly acidic taste.

Conclusion

This example demonstrates that granulating sodium bicarbonate lowers the amount of precipitate formed and still provides for quick dissolution time of the tablet.

Example 17: Effervescent Tablet with Granulation of Sodium Bicarbonate at Lower Level Dried Manganese chloride tetrahydrate (from example 16), Alanine, Sodium bicarbonate granulate (from example 16), Citric acid anhydrate and PEG6000 were mixed for 5 minutes. Magnesium stearate was added and mixed for 1 minute. Tablets were compressed on a single punch tablet press using 20 mm flat faced tooling with a tablet weight of 2420 mg and a hardness of 85N. Content of Manganese chloride tetrahydrate was 800 mg/tablet, content of Alanine was 500 mg/tablet and content of Sodium bicarbonate was 281 mg/tablet. One tablet was put into a glass with 200 ml water at room temperature, and the tablet effervesced for about 3 minutes. A little precipitate of Manganese carbonate was formed (like examples 16), and after 4 minutes it was re-dissolved. The solution became opalescent and foaming. Adding even small amounts of Magnesium stearate made the solution look poor.

Example 18: Effervescent Tablet with Granulation of Sodium Bicarbonate at Low Level Dried Manganese chloride tetrahydrate (from example 16), Alanine, Dry Vitamin $D_3$ 100 SD/S, Sodium bicarbonate granulate (from example 16), Citric acid anhydrate and PEG6000 were mixed for 5 minutes. Tablets were compressed on a single punch tablet press using 20 mm flat faced tooling with a tablet weight of 2440 mg and a hardness of 80N. Content of Manganese chloride tetrahydrate was 800 mg/tablet, content of Alanine was 500 mg/tablet, content of Vitamin D was 20 µg/tablet plus 20% overage and content of Sodium bicarbonate was 253 mg/tablet. One tablet was put into a glass with 200 ml water at room temperature, and the tablet effervesced for about 3 minutes. A little precipitate of Manganese carbonate was formed (like example 16), and after 4 minutes it was re-dissolved giving a clear solution. Level of Sodium bicarbonate was reduced to slow down effervescence to reduce time from end effervescence to fully dissolved.

TABLE 4

Batch compositions for Example 15 to 18 in gram.

| | Example 15 | Example 16 | Example 17 | Example 18 |
|---|---|---|---|---|
| Manganese chloride tetrahydrate, dried | — | 16.4 | 16.4 | 16.4 |
| Manganese chloride/ citric acid granulate | 32.0 | — | — | — |
| Alanine | 12.5 | 12.5 | 12.5 | 12.5 |
| Dry Vitamin $D_3$ 100 SD/S | — | — | — | 0.24 |
| Sodium bicarbonate | 9.38 | — | — | — |
| Sodium bicarbonate granulate | — | 13.64 | 10.23 | 9.21 |
| Citric acid anhydrate | — | 15.0 | 15.0 | 15.0 |
| Isomalt | 2.39 | — | 2.66 | 4.1 |
| PEG6000 | 3.63 | 3.63 | 3.63 | 3.63 |
| Magnesium Stearate | — | — | 0.13 | — |
| Total | 59.9 | 61.1 | 60.49 | 61.0 |

Example 19: Comparison between "Effervescent Tablet" and "Stick Pack Formulation" on Time to Disintegrate and to Form a Clear Solution Depending on Temperature Materials Materials used in this investigation are listed below:
Effervescent tablets (c.f. Table 4): Batch RD1901-7-T1
Stick pack formulation containing the following for each dose:
 L-alanine—Batch: 1809009 (500 mg)
 Vitamin $D_3$ dry powder—Batch: 1809013 (10 mg)
 Manganese chloride tetrahydrate—Batch: 1912002 (800 mg)
Tap water The stick pack formulation is an oral dry powder formulation where manganese chloride tetrahydrate (800 mg) is packed in one stick pack and a homogeneous blend of L-alanine (500 mg) and dry vitamin $D_3$ powder (10 mg, corresponding to 800 IU) is packed in another stick pack.

The two-compartment form of manganese chloride tetrahydrate in one pack, and L-alanine and dry vitamin $D_3$ powder in another pack is referred to as the powder formulation herein.

The effervescent tablets used herein contain the following:

TABLE 4

Composition of effervescent tablets. Manganese chloride dihydrate (654.41 mg) is obtained from drying 800 mg manganese chloride tetrahydrate.

| Tablet composition | (%) | (mg) |
|---|---|---|
| Manganese chloride dihydrate* | 26.82 | 654.41 |
| L-alanine | 20.5 | 500.20 |
| Dry vitamin D3 powder, 100 000** | 0.39 | 9.52 |
| Sodium bicarbonate | 10.37 | 252.95 |
| Povidone | 0.69 | 16.94 |
| Citric acid anhydrate | 24.61 | 600.48 |
| Isomalt | 10.71 | 261.30 |
| PEG6000 | 5.96 | 145.42 |
| Total (in gram) | | 2.44 |

Temperature Impact on Disintegration Time and Time to Form a Clear Solution

Method

The two different formulations, i.e. effervescent tablets and powder formulation, were dissolved in 200 ml of water at three different temperatures 5° C., 15° C. and 20° C. No stirring was used for the effervescent tablet, whereas the powder formulation was stirred. The time for disintegration (few visual particles) and time to clear solution (no visual particles) was measured. Three samples were tested for each formulation and temperature.

Results

The results from the test are presented in Table 5. It should be noted that disintegration is only applicable for the effervescent tablet. FIG. 1 shows the temperature impact on the disintegration time and time to form a clear solution for effervescent tablets. At every temperature tested, the effervescent tablet disintegrated and completely dissolved more rapidly than the powder formulation. Further, the lower the temperature, the longer the time for disintegration and complete dissolution.

TABLE 5

Time for disintegration and to a clear solution at different temperatures for the effervescent tablet and powder formulation (volume 200 ml).

| | | Effervescent tablet | | Powder formulation | |
|---|---|---|---|---|---|
| Temp. | Test no | Time for disintegration (minutes) | Time for clear solution (minutes) | Time for disintegration (minutes) | Time for clear solution (minutes) |
| 5° C. | 1 | 4:02 | 7:24 | N/A | 10:11 |
| | 2 | 4:16 | 7:34 | N/A | 10:17 |
| | 3 | 4:19 | 7:54 | N/A | 10:15 |
| | Average | 4:12 | 7:37 | N/A | 10:14 |
| 15° C. | 1 | 3:15 | 5:25 | N/A | 6:58 |
| | 2 | 3:17 | 5:10 | N/A | 7:50 |
| | 3 | 3:15 | 5:50 | N/A | 8:08 |
| | Average | 3:15 | 5:28 | N/A | 7:38 |
| 20° C. | 1 | 3:10 | 4:39 | N/A | 10:01 |
| | 2 | 2:50 | 4:54 | N/A | 10:30 |
| | 3 | 3:01 | 4:20 | N/A | 10:16 |
| | Average | 3:00 | 4:37 | N/A | 10:15 |

N/A = Not applicable.

Conclusions

The test demonstrates that the effervescent tablet of the present disclosure disintegrates faster than 5 minutes in 0.2 L of water at a temperature between 5° C. and 20° C. with a faster disintegration at the higher temperatures. A temperature of 5° C. is preferred from a patient perspective, since a 5° C. water solution is more pleasant to drink. This test demonstrates also that the time to dissolve the effervescent tablet is significantly shorter than the time to dissolve the powder formulation. Hence, a compressed solid composition performs better than the powder formulation in the context of preparing an oral solution for use in MRI.

Example 20: Comparison between "Effervescent Tablet" and "Stick Pack Formulation" on Time to Disintegrate and to Form a Clear Solution Depending on Volume Method The two different formulations, i.e. effervescent tablet and powder formulation of Example 19, were dissolved in 50 ml or 200 ml of 20° C. water. No stirring was used for the effervescent tablet, whereas the powder formulation was stirred. The time for disintegration (few visual particles) and time to clear solution (no visual particles) was measured. Three samples were tested for each formulation at different volumes.

Results

Figure 2:
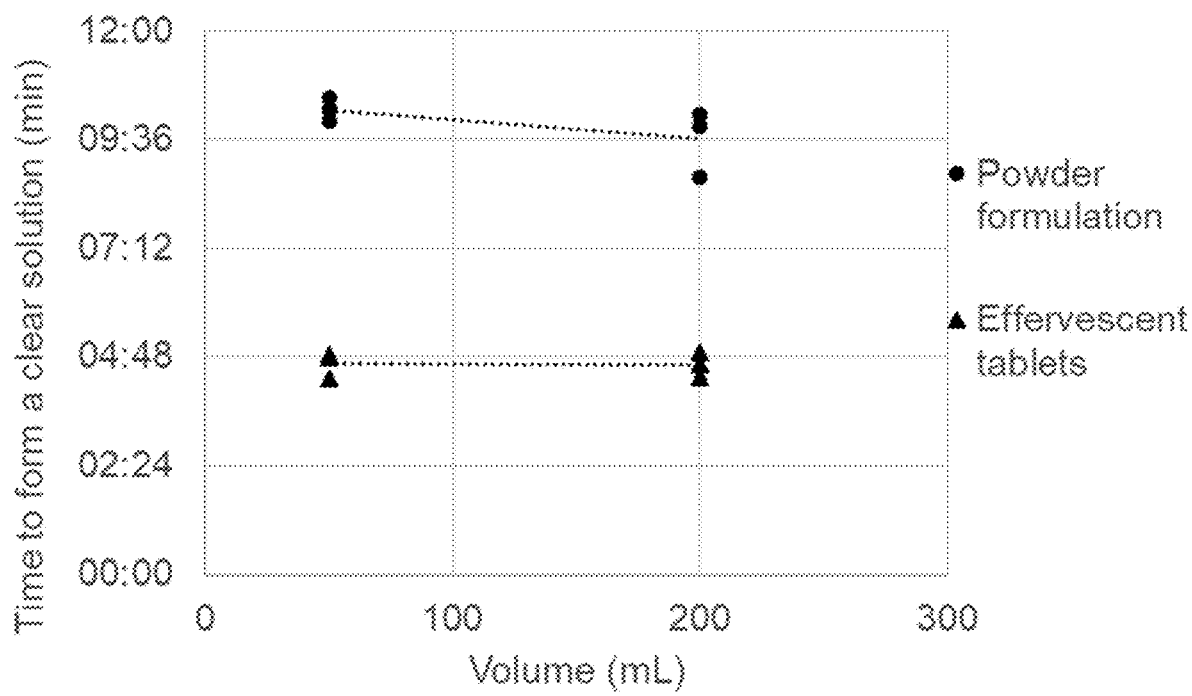
FIG. 2: Time for disintegration into a clear solution at different volumes of water for the effervescent tablet and two-compartment powder formulation, respectively (at 20° C.). The effervescent tablet displays significantly faster and thus superior dissolution and disintegration rates compared to the two-compartment powder formulation.
Figure 3A:
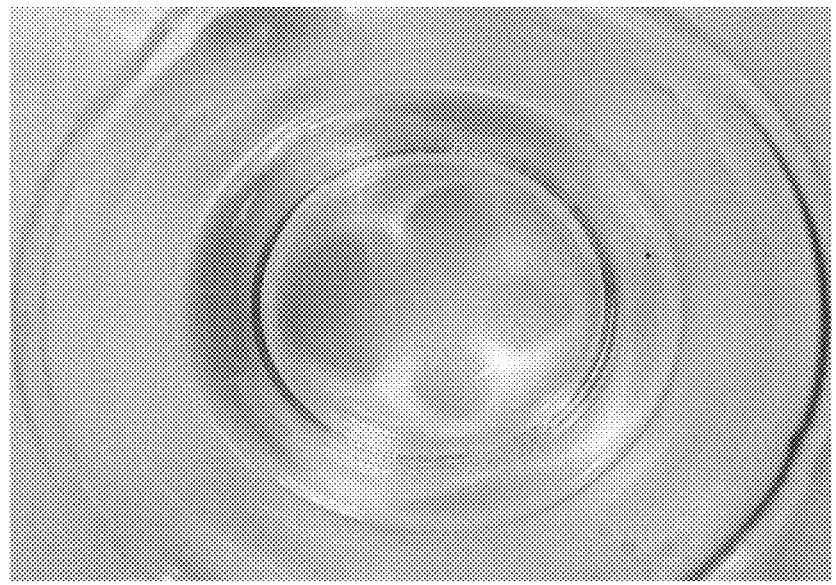
FIGS. 3A and 3B show visual examination of a glass of water into which an effervescent tablet (FIG. 3A) or two-compartment powder formulation (FIG. 3B) has been subjected.
Figure 3B:
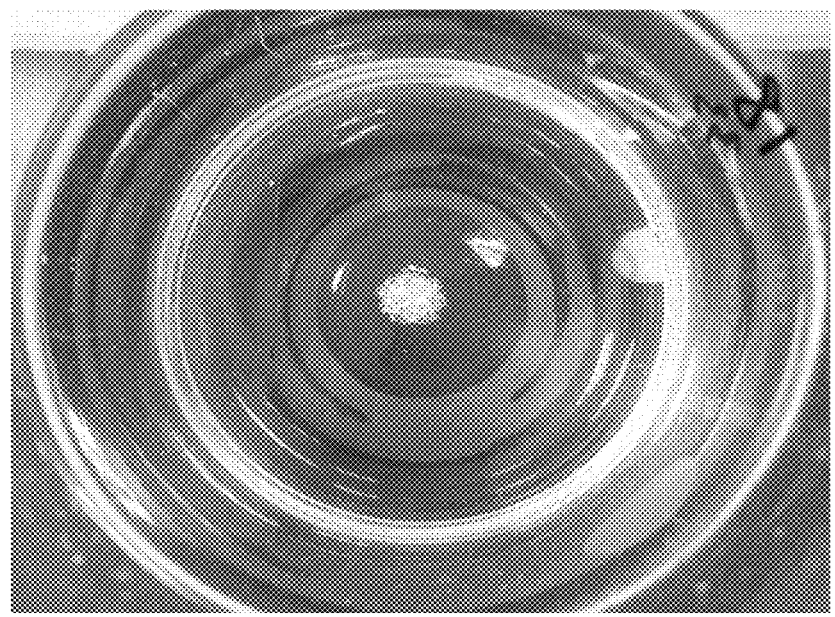

The results are presented in Table 6. It should be noted that disintegration is only applicable for the effervescent tablet. In FIG. 2 the impact on the water volume is shown. As can be seen from the results the volume in the investigated range does not have an impact on neither the time for disintegration of time to form a clear solution. The effervescent tablets have formed a clear solution whereas the powder formulation has undissolved particles.

TABLE 6

Time for disintegration and to a clear solution at different volumes for the effervescent tablet and powder formulation (at 20° C.).

| | | Effervescent tablet | | Powder formulation | |
|---|---|---|---|---|---|
| Volume | Test no | Time for disintegration (minutes) | Time for clear solution (minutes) | Time for disintegration (minutes) | Time for clear solution (minutes) |
| 50 mL | 1 | 2:56 | 4:47 | N/A | 10:01 |
| | 2 | 2:55 | 4:19 | N/A | 10:31 |
| | 3 | 3:05 | 4:50 | N/A | 10:16 |
| | Average | 2:58 | 4:38 | N/A | 10:16 |
| 200 mL | 1 | 3:10 | 4:39 | N/A | 8:46 |
| | 2 | 2:50 | 4:54 | N/A | 9:54 |
| | 3 | 3:01 | 4:21 | N/A | 10:10 |
| | Average | 3:00 | 4:38 | N/A | 9:36 |

N/A = Not applicable.

The results in Table 6 show the differences between the two formulations after 5 minutes in either 50 ml or 200 mL of 20° C. tap water.

Conclusions

This example demonstrates that a compressed solid composition (e.g. an effervescent tablet) display significantly faster and thus superior dissolution and disintegration rates compared to the two-compartment powder formulation. Hence, a compressed solid composition performs better than the powder formulation in the context of preparing an oral solution for use in MRI. Further, a volume between 50 mL and 200 mL does not have any significant impact on the time for disintegration/dissolution.

The invention claimed is:

1. An effervescent MRI tablet for magnetic resonance imaging (MRI) comprising:
   a) in the range of 0.50 g to 1.2 g manganese (II) chloride tetrahydrate or an equimolar amount of the corresponding anhydrate or dihydrate;
   b) in the range of 0.25 g to 0.75 g of L-alanine;
   c) one or more water-soluble excipients; and
   d) an effervescent couple comprising a basic ingredient and an acidic ingredient;
   wherein the effervescent tablet is for preparing an oral solution for use in MRI.

2. The effervescent MRI tablet according to claim 1, wherein the one or more water-soluble excipients are selected from the group consisting of: a non-hygroscopic filler, a non-hygroscopic binder, a non-hygroscopic disintegrant, a non-hygroscopic lubricant, and combinations thereof.

3. The effervescent MRI tablet according to claim 2 comprising the non-hygroscopic filler, wherein the non-hygroscopic filler is selected from the group consisting of: isomalt; lactose; maltitol; maltose; and mannitol.

4. The effervescent MRI tablet according to claim 2 comprising the non-hygroscopic binder, wherein the non-hygroscopic binder is selected from the group consisting of: hydroxyethylmethyl cellulose; maltose; povidone; and dextrin.

5. The effervescent MRI tablet according to claim 2 comprising the non-hygroscopic disintegrant povidone.

6. The effervescent MRI tablet according to claim 2 comprising the non-hygroscopic lubricant, wherein the non-hygroscopic lubricant is selected from the group consisting of: polyethylene glycol 6000; and sodium benzoate.

7. The effervescent MRI tablet according to claim 1, wherein the effervescent MRI tablet further comprises vitamin $D_3$.

8. The effervescent MRI tablet according to claim 1, wherein the effervescent MRI tablet comprises 0.50 g L-alanine.

9. The effervescent MRI tablet according to claim 1, wherein the effervescent MRI tablet provides a clear solution in 0.2 L water at room temperature within 5 minutes or less without stirring or agitation of the solution.

10. The effervescent MRI tablet according to claim 1, wherein the effervescent MRI tablet completely dissolves in water at room temperature within 5 minutes or less without stirring or agitation of the solution.

11. The effervescent MRI tablet according to claim 1, wherein the effervescent MRI tablet disintegrates within less than 3.0 minutes in 0.2 L water at room temperature without any stirring or agitation of the solution.

12. The effervescent MRI tablet according to claim 1, wherein the effervescent MRI tablet results in a pH of between 2 to 7 in 0.2 L water after complete dissolution of between 0.5 g and 1 g manganese (II) chloride tetrahydrate or an equimolar amount of the corresponding anhydrate or dihydrate.

13. The effervescent MRI tablet according to claim 1, wherein the effervescent MRI tablet has a mass in the range of 1.8 g to 4.0 g.

14. The effervescent MRI tablet according to claim 1, wherein the effervescent MRI tablet comprises granulated bicarbonate.

15. The effervescent MRI tablet according to claim 1, wherein the effervescent MRI tablet comprises citric acid.

16. The effervescent MRI tablet according to claim 1, comprising citric acid and sodium bicarbonate, wherein a mass ratio between the citric acid and the sodium bicarbonate in the effervescent MRI tablet is 1.2 to 1.

17. The effervescent MRI tablet according to claim 1, wherein the effervescent MRI tablet comprises:
   a. Manganese chloride tetrahydrate, dihydrate, or anhydrate;
   b. L-Alanine;
   c. Isomalt;
   d. Sodium bicarbonate;
   e. Citric acid; and
   f. PEG6000.

18. The effervescent MRI tablet according to claim 1, wherein the effervescent MRI tablet consists of:
   a. Manganese chloride tetrahydrate, dihydrate, or anhydrate;
   b. L-Alanine;
   c. Isomalt;
   d. Sodium bicarbonate;
   e. Citric acid;
   f. PEG6000;
   g. Povidone; and
   h. Vitamin $D_3$.

* * * * *